(12) United States Patent
Krishna et al.

(10) Patent No.: US 9,747,421 B2
(45) Date of Patent: Aug. 29, 2017

(54) MULTI-FACTOR BRAIN ANALYSIS VIA MEDICAL IMAGING DECISION SUPPORT SYSTEMS AND METHODS

(71) Applicant: Picofemto LLC, New York, NY (US)

(72) Inventors: Srikant Krishna, Stamford, CT (US); Fatih Sirin, New York, NY (US); Dhinakaran Chinappen, Sunnyside, NY (US); Robert Callan, New York, NY (US); William C. Bubel, Bronx, NY (US); Brian Kennedy, Cortlandt Manor, NY (US)

(73) Assignee: Picofemto LLC, New York, NY (US)

( * ) Notice: Subject to any disclaimer, the term of this patent is extended or adjusted under 35 U.S.C. 154(b) by 0 days.

(21) Appl. No.: 14/617,708

(22) Filed: Feb. 9, 2015

(65) Prior Publication Data
US 2015/0227702 A1    Aug. 13, 2015

Related U.S. Application Data

(60) Provisional application No. 61/937,982, filed on Feb. 10, 2014.

(51) Int. Cl.
| | |
|---|---|
| *G06Q 50/22* | (2012.01) |
| *G06F 19/00* | (2011.01) |
| *A61B 5/04* | (2006.01) |
| *A61B 5/048* | (2006.01) |
| *A61B 5/00* | (2006.01) |

(Continued)

(52) U.S. Cl.
CPC ........... *G06F 19/345* (2013.01); *A61B 5/048* (2013.01); *A61B 5/04012* (2013.01); *A61B 5/4094* (2013.01); *A61B 5/7257* (2013.01); *G06F 19/321* (2013.01); *A61B 5/055* (2013.01); *A61B 5/743* (2013.01); *G01R 33/4808* (2013.01); *G01R 33/546* (2013.01); *G01R 33/5608* (2013.01)

(58) Field of Classification Search
CPC .................. G06Q 50/22–50/24; G06F 19/345
See application file for complete search history.

(56) References Cited

U.S. PATENT DOCUMENTS

| | | | | |
|---|---|---|---|---|
| 8,873,836 B1 * | 10/2014 | Dietrich | ............... | G06K 9/6267 382/155 |
| 2002/0164059 A1 | 11/2002 | DiFilippo et al. | | |

(Continued)

FOREIGN PATENT DOCUMENTS

| | | |
|---|---|---|
| WO | WO-2008/052283 | 5/2008 |
| WO | WO-2011/127609 | 10/2011 |
| WO | WO-2011/146994 | 12/2011 |

OTHER PUBLICATIONS

International Search Report and Written Opinion for International Application No. PCT/US2015/015050, dated Jun. 25, 2015, 11 pages.

*Primary Examiner* — Robert Sorey
(74) *Attorney, Agent, or Firm* — Foley & Lardner LLP

(57) ABSTRACT

A medical imaging decision support system is provided that can conduct, and help medical professionals conduct multi-factor brain analysis. Data for disparate processing modes (for example, EEG, MRI, etc.) can be input to the system, processed in parallel in a cloud environment, and the results can be rendered in a thin client (for example, browser) for a user's rapid multi-modal evaluation of a brain.

10 Claims, 20 Drawing Sheets

(51) Int. Cl.
   *A61B 5/055*   (2006.01)
   *G01R 33/48*   (2006.01)
   *G01R 33/54*   (2006.01)
   *G01R 33/56*   (2006.01)

(56) References Cited

U.S. PATENT DOCUMENTS

| | | | |
|---|---|---|---|
| 2003/0181821 A1* | 9/2003 | Greenwald | A61B 5/048 600/544 |
| 2004/0092809 A1* | 5/2004 | DeCharms | G01R 33/4806 600/410 |
| 2004/0097802 A1* | 5/2004 | Cohen | A61B 5/04004 600/411 |
| 2006/0274885 A1* | 12/2006 | Wang | G06Q 50/22 378/65 |
| 2008/0008366 A1 | 1/2008 | Desh et al. | |
| 2009/0213034 A1* | 8/2009 | Wu | G06F 19/321 345/1.1 |
| 2012/0221728 A1 | 8/2012 | Dubbels et al. | |
| 2013/0204122 A1* | 8/2013 | Hendler et al. | 600/411 |
| 2013/0208955 A1* | 8/2013 | Zhao et al. | 382/128 |
| 2013/0218043 A1* | 8/2013 | Yoshida | 600/544 |
| 2013/0322722 A1* | 12/2013 | Vija | G06F 19/321 382/131 |

\* cited by examiner

```xml
<?xml version="1.0" encoding="utf8"
?>
<AnalyticModule
Name="EEG Time Chunk Analytic Workflow"
Identifier="EEGTimeChunkAnalysis"
Version="0.2"
Description="EEG Time Chunk Data Analysis Plugin"
DependencyStrategy="Picofemto.AnalyticPlugins.EEGTimeChunk.DependencyStrategy,
Picofemto.AnalyticPlugins.EEGTimeChunk">
<InputTypes>
<InputType Name="Single File EDF" Key="SingleFileEDF" Description="EDF data format, single file" Enabled="true">
<File Label="EDF+ Data File" Key="EDFFile" Description="EDF Data File" MinCount="1" MaxCount="1">
<Criteria Property="FileKey" Value="EDF" MatchType="Equals" ValidationMessage="File type must be EDF"/>
</File>
</InputType>
<InputType Name="EDF Plus Position Data" Key="EDFPlusPosition" Description="EDF data file plus sensor position" Enabled="true">
<File Label="EDF+ Data File" Key="EDFFile" Description="EDF Data File" MinCount="1" MaxCount="1">
<Criteria Property="FileKey" Value="EDF" MatchType="Equals" ValidationMessage="File type must be EDF"/>
</File>
<File Label="EEG Position Data" Key="PositionFile" Description="Contains sensort position data" MinCount="1" MaxCount="1">
<Criteria Property="FileKey" Value="EEGPOSITION"
MatchType="Equals" ValidationMessage="File type must be
EEGPOSITION"/>
</File>
</InputType>
</InputTypes>
<Assets>
<Global>
<GlobalAsset Mimetype="text/css" Name="Styles.JQueryUI" Version="1.10.3" />
<GlobalAsset Mimetype="text/css" Name="Picofemto.Styles.CoherenceMap" Version="0.0.1" />
<GlobalAsset Mimetype="text/css" Name="Picofemto.Styles.EEGChart" Version="0.0.1" />
<GlobalAsset Mimetype="text/css" Name="Picofemto.Styles.IncidentTimeline" Version="0.0.1" />
<GlobalAsset Mimetype="text/css" Name="Picofemto.Styles.WaveletSubBandChart" Version="0.0.1" />
<GlobalAsset Mimetype="text/css" Name="Picofemto.Styles.ComponentPowerFrequency" Version="0.0.1" />
<GlobalAsset Mimetype="text/css" Name="Picofemto.Styles.PowerSpectrumChart" Version="0.0.1" />
<GlobalAsset Mimetype="text/css" Name="Styles.DataTables" Version="0.0.1" />
<GlobalAsset Mimetype="text/javascript" Name="PicofemtoCommon" Version="0.0.1"/>
<GlobalAsset Mimetype="text/javascript" Name="PicofemtoEEGChartAPI" Version="0.0.1"/>
<GlobalAsset Mimetype="text/javascript" Name="PicofemtoIncidentListingAPI" Version="0.0.1"/>
<GlobalAsset Mimetype="text/javascript" Name="PicofemtoWaveletSubBandAPI" Version="0.0.1"/>
<GlobalAsset Mimetype="text/javascript" Name="Picofemto.Scripts.Waveform.EEG.Sorting" Version="0.0.1"/>
<GlobalAsset Mimetype="text/javascript" Name="Picofemto.Scripts.HeatMapExplorer" Version="0.0.1"/>
<GlobalAsset Mimetype="text/javascript" Name="Picofemto.Scripts.CoherenceMap" Version="0.0.1"/>
<GlobalAsset Mimetype="text/javascript" Name="Picofemto.Scripts.ColorScaleExplorer" Version="0.0.1"/>
<GlobalAsset Mimetype="text/javascript" Name="Picofemto.Scripts.ComponentPowerFrequencyExplorer" Version="0.0.1"/>
<GlobalAsset Mimetype="text/javascript" Name="Picofemto.Scripts.WaveletSubbandChartExplorer" Version="0.0.1"/>
<GlobalAsset Mimetype="text/javascript" Name="Picofemto.Scripts.IncidentTimeline" Version="0.0.1"/>
<GlobalAsset Mimetype="text/javascript" Name="Picofemto.Scripts.EEGChartExplorer" Version="0.0.1"/>
<GlobalAsset Mimetype="text/javascript" Name="Picofemto.Scripts.PowerSpectrumAPI" Version="0.0.1"/>
<GlobalAsset Mimetype="text/javascript" Name="Picofemto.Scripts.PowerSpectrumChartExplorer" Version="0.0.1"/>
<GlobalAsset Mimetype="text/javascript" Name="Picofemto.Scripts.PowerSpectrumReport" Version="0.0.1"/>
<GlobalAsset Mimetype="text/javascript" Name="EEGIncidentReport" Version="0.0.1"/>
<GlobalAsset Mimetype="text/javascript" Name="Picofemto.Scripts.CoherenceReport" Version="0.0.1"/>
<GlobalAsset Mimetype="text/javascript" Name="D3" Version="3.3.6" />
<GlobalAsset Mimetype="text/javascript" Name="KnockOut" Version="2.3.0"/>
<GlobalAsset Mimetype="text/javascript" Name="JQuery" Version="1.9.1"/>
<GlobalAsset Mimetype="text/javascript" Name="JQueryMigrate" Version="1.1.1"/>
<GlobalAsset Mimetype="text/javascript" Name="JQueryUI" Version="1.10.3"/>
<GlobalAsset Mimetype="text/javascript" Name="JQueryBlockUI" Version="2.66.0"/>
<GlobalAsset Mimetype="text/javascript" Name="DataTables" Version="0.0.1"/>
</Global>
```

FIG. 8

```
<Private>
<PrivateAsset Name="EEGVisualizer"
Mimetype="application/javascript" Location="Visualizers/picofemto.eeg.visualizer.js"
External="true"/>
<PrivateAsset Name="D3Script" Mimetype="application/javascript" Location="Resources/Scripts/d3.v3.min.js"
External="true"/>
<PrivateAsset Name="EEGChannelChartScript" Mimetype="application/javascript"
Location="Resources/Scripts/EEGChannelsChart.js" External="true"/>
<PrivateAsset Name="ReportTemplate" Mimetype="text/html" Location="Resources/Templates/Report.html"
External="true"/>
<PrivateAsset Name="CoherenceReportTemplate" Mimetype="text/html"
Location="Resources/Templates/CoherenceReportTemplate.html" External="true"/>
<PrivateAsset Name="VarianceSeizureDetectionReportTemplate" Mimetype="text/html"
Location="Resources/Templates/VarianceSeizureDetectionReportTemplate.html" External="true"/>
<PrivateAsset Name="ICALocalizationReportTemplate" Mimetype="text/html"
Location="Resources/Templates/ICALocalizationReportTemplate.html" External="true"/>
<PrivateAsset Name="PowerSpectrumReportTemplate" Mimetype="text/html"
Location="Resources/Templates/PowerSpectrumReportTemplate.html" External="false"/>
<PrivateAsset Name="StandardLocationFile" Mimetype="text/plain" Location="Resources/Files/Standard1020Cap81.
ced"
External="true"/>
</Private>
</Assets>
<!===
Module Resource File Whitelist === >

<!===
Data Visualizers === >
<Visualizers>
<Visualizer Name="EEGVisualizer"
Label="EEG Visualizer" Asset="EEGVisualizer"
EntryPoint="eegvisualizer">
<Inputs>
<Param Name="WorkflowId" />
<Param Name="DefaultMode" />
</Inputs>
</Visualizer>
</Visualizers>
<!===
Data Inspectors === >
<Inspectors>
<Inspector Name="SeizureIncidentListing"
Type="Picofemto.AnalyticPlugins.EEGTimeChunk.Inspectors.IncidentListing.IncidentListingInspector,
Picofemto.AnalyticPlugins.EEGTimeChunk">
<Command Name="GetIncidents" Alias="GetIncidents" />
</Inspector>
<Inspector Name="CoherenceMap"
Type="Picofemto.AnalyticPlugins.EEGTimeChunk.Inspectors.CoherenceMap.CoherenceInspector,
Picofemto.AnalyticPlugins.EEGTimeChunk">
<Command Name="GetSubbandData" Alias="GetSubbandData" />
</Inspector>
<Inspector Name="EEGChart"
Type="Picofemto.AnalyticPlugins.EEGTimeChunk.Inspectors.EEGChart.EEGChartInspector,
Picofemto.AnalyticPlugins.EEGTimeChunk">
<Command Name="GetEEGData" Alias="FetchData" />
</Inspector>
<Inspector Name="ICAComponentMap"
Type="Picofemto.AnalyticPlugins.EEGTimeChunk.Inspectors.ICAComponentMap.ICAComponentMapInspector,
Picofemto.AnalyticPlugins.EEGTimeChunk">
<Command Name="GetData" Alias="FetchData" />
<Command Name="GetImage" Alias="GetHeatMapImage" />
</Inspector>
<Inspector Name="ICAPowerFrequency"
Type="Picofemto.AnalyticPlugins.EEGTimeChunk.Inspectors.ICAPowerFrequency.ICAPowerFrequencyInspector,
Picofemto.AnalyticPlugins.EEGTimeChunk">
<Command Name="GetData" Alias="FetchData" />
</Inspector>
```

FIG. 8 (contd.)

```xml
<Inspector Name="PowerSpectrum"
Type="Picofemto.AnalyticPlugins.EEGTimeChunk.Inspectors.PowerSpectrum.PowerSpectrumInspector,
Picofemto.AnalyticPlugins.EEGTimeChunk">
<Command Name="GetData" Alias="GetPowerSpectrum" />
</Inspector>
<Inspector Name="WaveletSubBand"
Type="Picofemto.AnalyticPlugins.EEGTimeChunk.Inspectors.WaveletSubBand.WaveletSubBandInspector,
Picofemto.AnalyticPlugins.EEGTimeChunk">
<Command Name="GetData" Alias="GetSubBands" />
</Inspector>
</Inspectors>
<!===
Report Generation Parameters === >
<Reports>
<Report
Name="EEGReport"
Description="report generation"
Formatter="Picofemto.AnalyticPlugins.EEGTimeChunk.Reports.EEGRenderer, Picofemto.AnalyticPlugins.EEGTimeChunk"
Configuration="Picofemto.AnalyticPlugins.EEGTimeChunk.Reports.EEGRendererConfig,
Picofemto.AnalyticPlugins.EEGTimeChunk">
<Parameter Name="GeneratedReportName" Value="Channel Summary Report" />
<Parameter Name="WaveformFileKey" Value="EDFFile" />
</Report>
<Report
Name="VarianceSeizureDetectionReport"
Description="seizure detection report generation"
Formatter="Picofemto.AnalyticPlugins.EEGTimeChunk.Reports.VarianceSeizureDetectionRenderer,
Picofemto.AnalyticPlugins.EEGTimeChunk"
Configuration="Picofemto.AnalyticPlugins.EEGTimeChunk.Reports.VarianceSeizureDetectionRendererConfig,
Picofemto.AnalyticPlugins.EEGTimeChunk">
<Parameter Name="GeneratedReportName" Value="Seizure Detection" />
<Parameter Name="WaveformFileKey" Value="EDFFile" />
</Report>
<Report
Name="CoherenceReport"
Description="Coherenece Report Generation"
Formatter="Picofemto.AnalyticPlugins.EEGTimeChunk.Reports.CoherenceRenderer,
Picofemto.AnalyticPlugins.EEGTimeChunk"
Configuration="Picofemto.AnalyticPlugins.EEGTimeChunk.Reports.CoherenceRendererConfig,
Picofemto.AnalyticPlugins.EEGTimeChunk">
<Parameter Name="GeneratedReportName" Value="Channel Coherence" />
</Report>
<Report
Name="ICALocalization"
Description="ICA Localization"
Formatter="Picofemto.AnalyticPlugins.EEGTimeChunk.Reports.ICALocalizationRenderer,
Picofemto.AnalyticPlugins.EEGTimeChunk"
Configuration="Picofemto.AnalyticPlugins.EEGTimeChunk.Reports.ICALocalizationRendererConfig,
Picofemto.AnalyticPlugins.EEGTimeChunk">
<Parameter Name="GeneratedReportName" Value="Component Localization" />
</Report>
<Report
Name="PowerSpectrumReport"
Description="Power Spectrum Report"
Formatter="Picofemto.AnalyticPlugins.EEGTimeChunk.Reports.PowerSpectrumRenderer,
Picofemto.AnalyticPlugins.EEGTimeChunk"
Configuration="Picofemto.AnalyticPlugins.EEGTimeChunk.Reports.PowerSpectrumRendererConfig,
Picofemto.AnalyticPlugins.EEGTimeChunk">
<Parameter Name="GeneratedReportName" Value="Power Spectrum" />
<Parameter Name="WaveformFileKey" Value="EDFFile" />
</Report>
</Reports>
```

FIG. 8 (contd.)

```
<!===
Processing Steps === >
<Steps>
<AnalyticStep
Name="FirstLayer"
Type="Picofemto.AnalyticPlugins.EEGTimeChunk.Steps.PreprocessingStep, Picofemto.AnalyticPlugins.EEGTimeChunk"
SerializationStrategy="Picofemto.AnalyticPlugins.EEGTimeChunk.PreprocessingStepSerializer,
Picofemto.AnalyticPlugins.EEGTimeChunk"
MaxmimumProcessingTimeInSeconds="120">
<Parameter Name="PerformFiltering" Value="true" />
<Parameter Name="ChannelDownsampleRate" Value="256" />
<Parameter Name="VarianceDownsampleRate" Value="4" />
<Parameter Name="WaveformFileKey" Value="EDFFile" />
<Parameter Name="PerformDownsample" Value="true" />
<Parameter Name="IgnoredChannels" Value="ECG" />
</AnalyticStep>
<AnalyticStep
Name="SecondLayer"
Type="Picofemto.AnalyticPlugins.EEGTimeChunk.Steps.WaveformProcessingStep, Picofemto.AnalyticPlugins.EEGTimeChunk"
SerializationStrategy="Picofemto.AnalyticPlugins.EEGTimeChunk.WaveformProcessingStepSerializer,
Picofemto.AnalyticPlugins.EEGTimeChunk">
<Parameter Name="PerformFiltering" Value="true" />
<Parameter Name="BandFilterOrder" Value="5" />
<Parameter Name="BandFilterLowerFrequency" Value="0.5" />
<Parameter Name="BandFilterUpperFrequency" Value="40" />
<Parameter Name="PerformDownsample" Value="true" />
<Parameter Name="VarianceWindowSize" Value="0.25" />
<Parameter Name="VarianceDownsampleRate" Value="4" />
<Parameter Name="ChannelDownsampleRate" Value="256" />
</AnalyticStep>
<AnalyticStep
Name="ThirdLayer"
Type="Picofemto.AnalyticPlugins.EEGTimeChunk.Steps.IncidentDetectionStep, Picofemto.AnalyticPlugins.EEGTimeChunk"
SerializationStrategy="Picofemto.AnalyticPlugins.EEGTimeChunk.IncidentDetectionStepSerializer,
Picofemto.AnalyticPlugins.EEGTimeChunk"
MaxmimumProcessingTimeInSeconds="300">
<Parameter Name="VarianceWindowSize" Value="0.25" />
</AnalyticStep>
</Steps>
</AnalyticModule>
```

FIG. 8 (contd.)

MULTI-FACTOR BRAIN ANALYSIS VIA MEDICAL IMAGING DECISION SUPPORT SYSTEMS AND METHODS

CROSS REFERENCE TO RELATED APPLICATION

This application claims the benefit of U.S. Provisional Application Ser. No. 61/937,982 filed Feb. 10, 2014, the disclosure of which is incorporated herein by reference in its entirety for all purposes.

BACKGROUND

Brain injuries, head traumas, concussions, and other head conditions can be difficult and time consuming to diagnose or evaluate. It can be difficult to determine whether the patient should return to activity after experiencing a head impact. In sports, for example, it is challenging and difficult to analyze whether the player who experienced the head impact should return to the game. Current procedures for evaluating such a patient are rudimentary. It is often not until the next day that a player's medical imaging evaluation can be completed. Multi-modal analysis is often not possible on a close-to-real time basis because the systems and methods for providing such a service simply do not exist or exist only in specialized environments. It is challenging and difficult to develop high performance brain injury analysis systems and user interfaces that provide for quality diagnostics away from a high end clinic environment.

SUMMARY

The present disclosure provides, in some embodiments, a multi-factor medical data decision support system, including: (1) an analysis server including an analysis manager and a web interface for communication with a client; (2) one or more analytic modules coordinated by the analysis manager for analyzing the medical data, wherein each of the one or more analytic modules is configured for independent loading and execution; and (3) a remote storage in data communication with the analysis server and the one or more analytic modules, wherein the remote storage stores at least one of measured medical data and processed medical data.

In some embodiments, each of the one or more analytic modules of the system is configured to be dynamically loaded into the system and updated independently.

In some embodiments, the one or more analytic modules of the system are configured to process the medical data at least partially in parallel.

In some embodiments, the system is configured to analyze at least one of structural medical data and functional medical data of an organ.

In some embodiments, each of the one or more analytic modules of the system is configured to analyze at least one of an electroencephalogram (EEG), magnetoencephalography (MEG), magnetic resonance image (MRI), electrocardiogram (ECG), computed tomography (CT), positron emission tomography (PET), and single-photon emission computed tomography (SPECT).

In some embodiments, at least one of the one or more analytic modules of the system is configured for combined analysis of two or more different types of medical data. In some embodiments, the at least one of the one or more analytic modules is configured for combined analysis of structural medical data and functional medical data of an organ to associate a source of an organ activity with a location in an anatomical structure of the organ. In some embodiments, the different types of medical data include EEG, MEG, ECG, MRI, CT, PET, and SPECT.

In some embodiments, the analysis manager of the analysis server in the system includes a scheduler configured to perform at least one of allocating a task to available resources, coordinating a sequence of analytic procedures in a workflow, and handling a failed analytic procedure. In some embodiments, the allocating of the task is based on at least one of priority, time received, and resource required; and coordinating the sequence of the analytic procedures in the workflow is at least partially based on dependencies between the analytic procedures.

In some embodiments, the web interface of the analysis server in the system is configured to provide graphical analysis results of at least one of the one or more analytic modules to the client automatically or upon request.

In some embodiments, the web interface of the analysis server in the system is configured to provide graphical analysis results of two or more of the one or more analytic modules together to the client for medical decision.

In some embodiments, each of the one or more analytic modules of the system includes one or more analytic workers each configured to perform a specific analysis, wherein each of the one or more analytic workers is configured to be independently loaded into one of the one or more analytic modules and independently executed. In some embodiments, the one or more analytic workers are configured to at least partially run in parallel. In some embodiments, the web interface of the analysis server in the system is configured to provide analysis results of the one or more analytic workers to the client on a single user interface at same time.

In some embodiments, one of the one or more analytic modules of the system is an EEG analysis module, and each of the one or more analytic workers of the EEG analysis module analyzes at least one of wavelet subbands, power spectrum, coherences between signals, independent components, component heat maps, and density spectral map of an EEG signal.

In some embodiments, at least a part of the system resides on one or more cloud servers as a virtual machine instance. In some embodiments, at least a part of the system runs with at least two virtual machine instances and is configured to be dynamically scaled in response to demand. In some embodiments, at least a part of the system resides on a client device.

The present disclosure also provides, in some embodiments, a cloud-based EEG analysis system, including: (1) an analysis server including an analysis manager and a web interface for communication with a client; (2) one or more analytic workers managed by the analysis manager for analyzing EEG data to generate at least one of wavelet subbands, power spectrum, coherences between signals, independent component analysis, component heat maps, and density spectral map of the EEG data; and (3) a remote storage in data communication with the analysis server and the one or more analytic workers, wherein the remote storage stores the EEG data and analysis results of the one or more analytic workers, wherein at least a part of the system resides on one or more cloud servers as a virtual machine instance. In some embodiments, at least a part of the system runs with at least two virtual machine instances and is configured to be dynamically scaled in response to demand.

In some embodiments, the cloud-based EEG analysis system further includes an analytic cluster configured to perform combined analysis of the EEG data and at least one of MRI data, CT data, MEG data and ECG data.

In some embodiments, the analysis manager in the analysis server of the cloud-based EEG analysis system is configured to break a task into parallel execution processes for distributed processing. In some embodiments, the analysis manager is configured to divide the EEG data into time sections and keep a manifest in the remote storage for parallel processing. In some embodiments, the analysis manager is configured to manage parallel channel data processing for two or more EEG channels. In some embodiments, the analysis manager is configured to divide data of each of the two or more EEG channels into time sections for parallel processing.

In some embodiments, the web interface in the analysis server of the cloud-based EEG analysis system is configured to provide analysis results of the one or more analytic workers to the client on a unified graphical user interface. In some embodiments, the analysis results are provided to the client in real time.

The present disclosure also provides, in some embodiments, a method for providing EEG decision support, including: (1) displaying a user selectable menu in a first portion of a user display for taking user input; (2) providing a selectable multi-level graphical temporal data of an EEG in a second portion of the user display; (3) providing a zoomed graphical view of selected temporal data in a third portion of the user display; and (4) reporting graphical analysis results of the selected temporal data in a fourth portion of the user interface, wherein the graphical analysis results include one or more of wavelet subbands, power spectrum, coherences between signals, independent component analysis, component heat maps, and density spectral map of the EEG.

In some embodiments, the method for providing EEG decision support further includes saving the graphical analysis results to a file. In some embodiments, the method further includes automatically highlighting an abnormal section of the graphical temporal data of the EEG. In some embodiments, the method further includes combining analysis results of a structural scan data with the graphical analysis results of the selected temporal data of the EEG for source physical localization. In some embodiments, the method further includes reporting a generalized seizure or interictal spike if detected.

In some embodiments of the method for providing EEG decision support, two or more graphical analysis results of the selected temporal data are reported on the user interface at same time to facilitate a medical decision, wherein the two or more graphical analysis results are updated when an option on one of the two or more graphical analysis results is changed. In some embodiments, the one or more graphical analysis results are reported in real time and are updated in real time when an option on one of the one or more graphical analysis results is changed. In some embodiments, graphical analysis results of multiple EEG channels are reported on the user interface at same time.

The present disclosure also provides, in some embodiments, a system for visualizing an EEG and features extracted from the EEG to support a medical decision, including: (1) a first window displaying a user selectable menu; (2) a second window providing a selectable multi-level graphical temporal data of the EEG; (3) a third window displaying a zoomed graphical view of selected temporal data; and (4) a fourth window providing graphical analysis results of the selected temporal data, wherein the graphical analysis results include at least one of wavelet subbands, power spectrum, coherences between signals, independent component analysis, component heat maps, and density spectral map of the EEG. In some embodiments, changing an option in one of the windows causes at least one of other windows to update automatically. In some embodiments, at least one of the windows allows the user to insert an annotation.

The present disclosure further provides, in some embodiments, an EEG based seizure diagnostic method, comprising: (1) receiving EEG data including signals from multiple channels; (2) optionally extracting duration and metadata from the EEG data; (3) optionally building a manifest and dividing the EEG data into time sections; (4) optionally down-sampling and cleaning the EEG data; (5) calculating a variance of signal from each of the multiple channels; and (6) detecting risk of seizure based on an average of the variance of signal from each of the multiple channels. In some embodiments, the EEG based seizure diagnostic method further includes highlighting time sections where a seizure is indicated for further analysis. In some embodiments, at least a part of the method is configured to execute in parallel.

Other aspects and embodiments of the disclosure are also contemplated. The foregoing summary and the following detailed description are not meant to restrict the disclosure to any particular embodiment but are merely meant to describe some embodiments of the disclosure.

BRIEF DESCRIPTION OF DRAWINGS

FIG. 8 illustrates an XML definition of various modules.

Figure 1A:
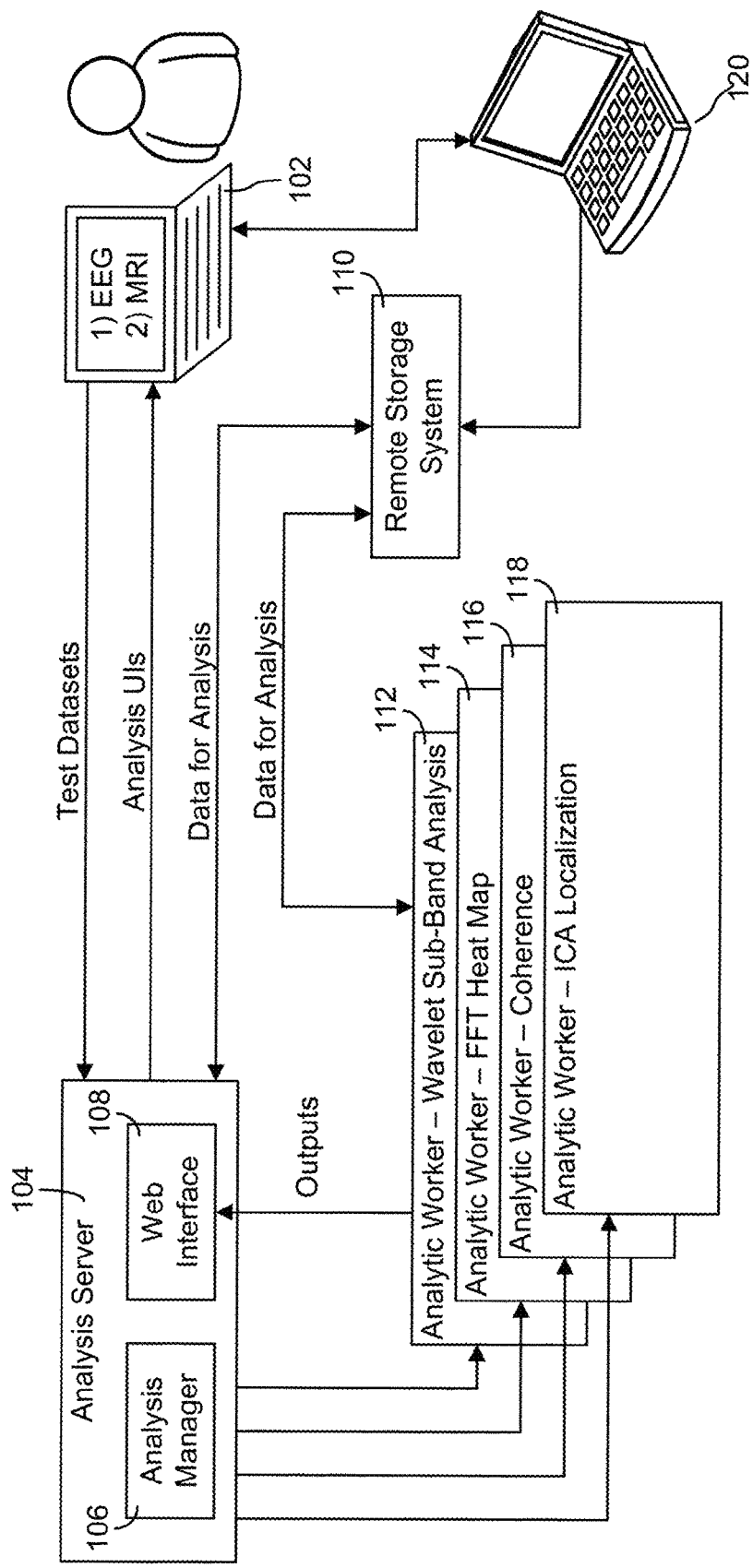
FIG. 1A illustrates a block diagram of a multi-factor medical analysis and decision support system.

Some or all of the figures are schematic representations by way of example; hence, they do not necessarily depict the actual relative sizes or locations of the elements shown, or the actual relative sequence or locations of the blocks shown. The figures are presented for the purpose of illustrating one or more embodiments with the explicit understanding that they will not be used to limit the scope or the meaning of the claims that follow below.

DETAILED DESCRIPTION

Before turning to the figures which illustrate the exemplary embodiments in detail, it should be understood that the application is not limited to the details or methodology set forth in the following description or illustrated in the figures. It should also be understood that the phraseology and terminology employed herein is for the purpose of description only and should not be regarded as limiting.

Referring generally to the Figures, multi-factor brain analysis systems and methods are shown and described. The systems and methods provide multi-factor imaging decision support. The systems and methods provide a computerized (for example, web-based) interface for allowing users to upload, analyze, save and retrieve data, and visualize data from anywhere around the globe (for example, using a web browser) to support a medical decision process. The interface can provide data and analysis from a cloud-based analysis system. The analysis system can conduct automatic and semi-automatic analysis spanning a plurality of modalities (i.e., analysis modes). Accordingly, the systems and methods of the present application can advantageously provide a cloud-based decision support system. The user interfaces and analysis that can be provided by the systems and methods described herein may be configured to combine analysis modes to provide valuable outputs (for example, graphical user interfaces, reports) that utilize information from the different analysis modes of the combination. For example, given a patient's dataset of EEG, MRI, and CT, combination analyses such as EEG-MRI, EEG-CT, MRI-CT, and EEG-MRI-CT can be provided by the outputs of the described systems and methods. These combinations may be provided even though, for example, EEG signals and MEG signals measure brain electrical activity at different temporal scales relative to functional magnetic resonance imaging (fMRI). It is envisioned that some of the systems and methods described herein may be used to combine structural scan data (MRI and CT scans show the morphometry of body organs) with an analysis of functional processes of organs (for example, as provided by PET or SPECT).

In an exemplary embodiment, the modality specific diagnostic and visualization logic can be provided by or executed by a plug-in architecture. The modality specific functions can be loaded into the system dynamically and can be loaded or upgraded independently. The plug-in architecture can advantageously provide enhanced flexibility, security, and reliability. The interaction with cloud storage and the workflow scheduling engine is mediated by communication or application interfaces that can allow for third parties to develop workflow diagnostic and analysis modules.

Referring now to FIG. 1A, a block diagram of a multi-factor medical analysis system is shown. As shown, the system can analyze EEG data, MEG data, and/or other medical imaging data for conducting a multi-factor brain analysis. The system is intended to rapidly provide the user's client machine 102 with output such as graphical user interfaces that can provide high quality and multi-modal decision support. In FIG. 1A, the client device 102 is shown as being a laptop. Advantageously, the system can take the processing load off the client device having the user interface and conduct the analysis on a cloud-based analysis system (for example, provided by the set of servers or subsystems spanning 104, 110, and 112-118).

Client device 102 can be a laptop computer or any other type of computing device. Client device 102 can execute a client application that can interact with analysis server 104. The client application may be a browser-based application such that the application is provided by a series of web-based or browser-based screens or graphical user interfaces. The client application may be provided using JavaScript, one or more of Java-Applet, dynamic HTML, XML, or other suitable standards, programming languages, or combinations thereof.

Although described in many places in this application as such a web-based or browser-based application, the client application may alternatively be a 'thick' client application configured for execution as a stand-alone or relatively stand-alone application. In many such embodiments, client device 102 may receive less logic and graphical user interface data from a remote source, but may still send and receive the imaging data, metadata, or result data described herein to and from the analysis server 104. In yet other embodiments, the analysis server (for example, the analysis manager) can be somewhat or fully integrated with a thick application running on the client device. Various claims presented in this or a future application may limit the claimed systems or methods to particular architectures.

Client device 102 can be used to send test datasets (for example, EEG and MRI datasets) to analysis server 104. This process is described in greater detail in FIG. 7. The analysis server 104 can receive the test datasets and send the test datasets to remote storage system 110.

In some embodiments, the medical analysis system includes one or more medical diagnostic machines 120. Medical diagnostic machine 120 may be one or more of an EEG machine, MRI machine, MEG machine, ECG machine, CT machine, PET machine, and SPECT machine. In some embodiments, medical diagnostic machine 120 is connected to client device 102 through wired or wireless network for real time data communication, such that real time medical analysis can be performed. In some embodiments, two or more medical diagnostic machines 120 may be connected to client device 102 via wired or wireless network for real time multi-factor medical analysis. In other embodiments, test datasets from medical diagnostic machine 120 can be transferred to client device 102 through machine-readable data storage media, such as CD-ROM, DVD-ROM or other optical data storage devices, magnetic disk storage or other magnetic storage devices, or non-volatile flash drive or other solid-state storage devices.

In some embodiments, medical diagnostic machine 120 communicates with remote storage system 110 to store medical diagnostic datasets on remote storage system 110 along with patient information. Client device 102 can identify the medical diagnostic datasets for analysis by searching remote storage system 110 using patient information. In some embodiments, medical diagnostic machine 120 can provide client device 102 with links or paths to the medical diagnostic datasets stored on remote storage system 110, and client device 102 can identify the medical diagnostic datasets for analysis using the links or paths to the stored medical diagnostic datasets.

Analysis server 104 can use an interface with remote storage system 110 to provide the test datasets to remote storage system 110. The datasets may then reside on remote storage system 110 for analytic processing. Once the data from the client device 102 is received and stored, the analysis server 104 can utilize a set of components, illustrated in FIG. 1A as an analysis manager 106, to execute a workflow appropriate for the test datasets or the client's goals. Different workflows may be stored in analysis manager 106 for different types of data, different client goals, different diagnostic approaches, or different combinations of modalities. Analysis manager 106 may schedule and execute the workflow. The workflow may have steps for execution in series as well as steps for execution in parallel. Analytic steps (whether configured for serial processing or parallel processing) can be executed in a distributed processing environment. In the example illustrated in FIG. 1A, a plurality of analytic workers 112-118 can be instantiated and executed in response to a workflow instruction for four parallel analytic processes to be conducted on the test datasets. In addition to this type of parallel processing, distributed processing may also be used to break any one analysis process into parallel execution processes. For example, the various channels of an EEG may each be processed in parallel to create the Fast Fourier Transform (FFT) heat map.

When an analytic worker has completed processing a portion of data, the result can be provided to the remote storage system 110 for storage. A message can be sent back to the analysis server 104 informing the analysis server 104 that a step of the process has completed. When the analysis server 104 has completed a workflow, the web interface 108 may draw data from the remote storage system 110 for use in generating a graphical user interface. The graphical user interface can be provided to client device 102. User interactions with the browser can result in requests for transformed data or new user interface features or data (for example, via user entered queries or selections). Such requests can be handled by the web interface 108. Some requests can trigger further analysis (for example, another analysis workflow can be recalled by analysis server 104 and coordinated by analysis manager 106). If the result or output data necessary to support a new user request is already available in the remote storage system 110, no such renewed analysis is necessary.

Figure 1B:
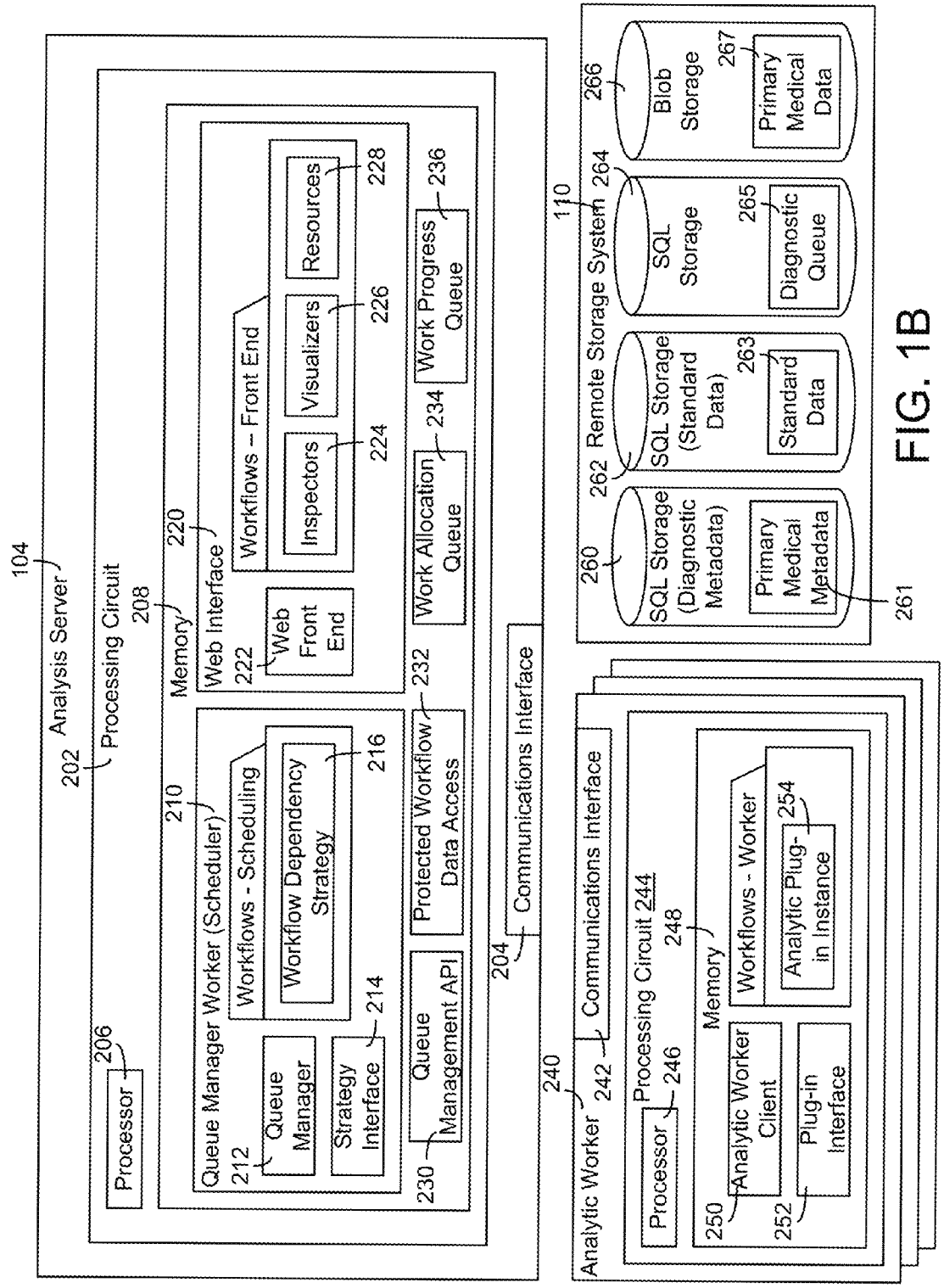
FIG. 1B illustrates a general architecture of the computer system of a multi-factor medical analysis system.

Referring to FIG. 1B, a general architecture of the computer system is shown, according to an exemplary embodiment. The computer system is shown to generally include an analysis server 104, analytic worker 240 and remote storage system 110. A part or all of the computer system may be hosted on a cloud server and run in a virtual machine instance. In some embodiments, a part or all of the computer system is run with at least two virtual machine instances to provide scalability and robustness. The system can be scaled in response to increased demand by increasing the number of machines dedicated to a specific function.

Analysis server 104 may generally be configured to receive requests from one or more clients 102 and to manage a queue of tasks to be executed by the computer system. Analysis server 104 is shown to generally include a processing circuit 202 including a processor 206 and memory 208. Analysis server is further shown to include a communications interface 204. Processor 206 may be implemented as a general purpose processor, an application specific integrated circuit (ASIC), one or more field programmable gate arrays (FPGAs), a group of processing components, or other suitable electronic processing components. Memory 208 may be one or more devices (for example, RAM, ROM, Flash memory, hard disk storage, etc.) for storing data and/or computer code for completing and/or facilitating the various processes described herein. Memory 208 may be or include non-transient volatile memory or non-volatile memory. Memory 208 may include database components, object code components, script components, or any other type of information structure for supporting the various activities and information structures described herein. Memory 208 may be communicably connected to processor 206 and may include computer code or instructions for executing one or more processes described herein. Communications interface 204 may be configured to facilitate communications between analysis server 104 and analytic workers 240 for processing the various tasks.

Analysis server 104 is shown to include a web interface 220. Web interface 220 may be configured to manage one or more interfaces provided to a client via a web browser (or other platform). Web interface 220 may receive client input via HTTP, for example. Web interface 220 is shown to include a web front end module 222 configured to receive input from the client and to process the client input for use by the computer system. After the client input has been processed by web front end module 222, a request from the client is identified from the input and is provided to queue management API 230. Queue management API 230 is configured to store the request in a queue for retrieval by a scheduler 210.

Web interface 220 is further shown to include workflow code for managing an interface provided for client 102. For example, web interface 220 is shown to include code relating to inspectors 224, visualizers 226 and resources 228. This code relating to inspectors 224, visualizers 226 and resources 228 may be used to interpret user input information at the web browser or other platform. The information may then be provided to scheduler 210 and to one or more databases via protected workflow data access 232. For example, code relating to inspectors 224, visualizers 226 and resources 228 may be configured to receive and handle medical data of a patient associated with the client input, and protected workflow data access 232 may be configured to provide the data to database 260 (for storing primary medical metadata 261) or to blob storage 266 (for storing primary medical data 267). Further, scheduler 210 may use the information to determine when to process the request provided by the client.

Analysis server 104 is shown to include a scheduler 210 (for example, a queue manager worker) in order to run analytic workloads efficiently and to coordinate dependencies between analytic steps in multi-step analytic workflows. In some embodiments, scheduler 210 includes two logical sections: (1) modality independent logic that provides queuing, load balancing, fault tolerance and progress tracking; and (2) modality specific logic that resolves dependencies between steps and determines which process steps to run. Scheduler 210 is configured to schedule tasks to be processed by the computer system. Scheduler 210 handles allocating tasks to analytic worker 240, tracking progress of analytic worker 240 and allocating new work as previously allocated work is done. Scheduler 210 may also retrieve tasks stored in diagnostic queue 265 stored by SQL storage 264.

Scheduler 210 is shown to include a queue manager 212 configured to manage diagnostic queue 265. Scheduler 210 further includes a strategy interface 214. Strategy interface 214 may define a strategy for how to schedule one or more tasks in a queue. For example, strategy interface 214 may define a strategy relating to which task should be scheduled first based on priority, time the task was received, or other properties. Queue manager 212 may use data from strategy interface 214 to help to determine the correct queue order and which task is to be processed next.

Queue manager 212 may further use a work allocation queue 234 and work progress queue 236 to schedule tasks. Work allocation queue 234 is a queue of tasks to be processed. Queue manager 212 may retrieve tasks from work allocation queue 234 and determine when to process the task and which resource should process the task. Work progress queue 236 may identify to queue manager 212 the progress of tasks currently being processed by various resources, which may allow queue manager 212 to predict which resources will soon become available, which resources can handle more tasks, etc.

Scheduler 210 may further include plug-in workflow code, shown as a workflow dependency strategy 216. Workflow dependency strategy 216 may determine a strategy for scheduling tasks (for example, how to schedule a task based on its priority, time received, and properties determined via code relating to inspectors 224, visualizers 226 and resources 228). Workflow dependency strategy 216 may be used by strategy interface 214 to define the strategy for task scheduling.

The computer system of FIG. 1B is shown to include a plurality of analytic workers 240. Analytic worker 240 may generally be configured to process the various tasks provided to analysis server 104. Each analytic worker may include a communications interface 242, processing circuit 244, processor 246 and memory 248 for general functionality as described below in the present disclosure.

Analytic worker 240 may include an analytic worker client 250, plug-in interface 252, and analytic plug-in instance 254 for processing the tasks. Analytic plug-in instance 254 is plug-in workflow code for processing the tasks. Analytic plug-in instance 254 may retrieve information from protected workflow data access 232 relating to the task. Analytic plug-in instance 254 may provide information to plug-in interface 252 relating to the task.

Analytic worker client 250 may provide information to work allocation queue 234 indicating a current workload of the analytic worker 240, and to work progress queue 236 indicating the progress of a current processed task. For example, analytic worker client 250 may indicate the failure or success of processing the task, and may indicate when the analytic worker 240 is ready for the next task, or otherwise.

In one embodiment, the computer system may include a work notification queue (not shown). The work notification queue may be used by queue manager 212 and protected workflow data access 232. For example, when a new task is received, queue manager 212 may receive such indication based on the task being added to the work notification queue using information from protected workflow data access 232.

The computer system of FIG. 1B includes remote storage system 110 configured to store data relating to the tasks. Remote storage system 110 includes database 260 configured to store diagnostic metadata. Database 260 may be a SQL database configured to store primary medical metadata 261. Primary medical metadata 261 may be metadata relating to tasks provided by the client.

In some embodiments, remote storage system 110 further includes a database 262 configured to store standard data 263. Database 262 may be a SQL database configured to store information from web front end 222. The information may be standard data relating to the task to be processed.

In some embodiments, remote storage system 110 further includes SQL storage database 264 configured to store diagnostic queue 265. Diagnostic queue 265 is configured to store a queue of tasks for retrieval by queue manager 212 as described above.

In some embodiments, remote storage system 110 further includes blob storage database 266 configured to store primary medical data 267. Primary medical data 267 may be data identified by a protected workflow data access 232 relating to a patient associated with the request or task.

Figure 1C:
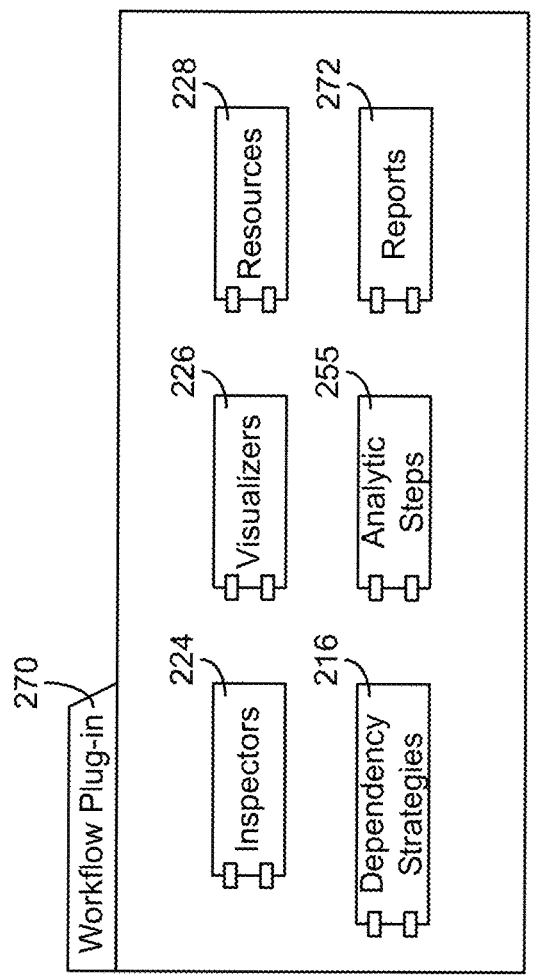
FIG. 1C illustrates various contents of a workflow plug-in module.

Referring now to FIG. 1C, various contents of workflow plug-in module 270 are shown. In FIG. 1B, the various contents are shown as part of scheduler 210, web interface 220, and analytic workers 240, distributed through the computer system as needed. As discussed above, inspectors 224 accept requests from web front end 222 during data visualization, permit data access and manipulation, and return the results to web front end 222. Visualizers 226 provide visualization for the results of the analysis. Resources 228 include data required for analysis (such as templates or tables), additional JavaScript for visualization, style sheets, or images. Resources 228 are accessible for back end data processing and for visualization. As described above, analytic steps 255 include steps to be executed in the workflow, such as, for example, data downsampling, bad channel detection, seizure detection, and image processing. Dependency strategies 216 determine which order to run analytic steps 255 in and coordinate all data processing for the workflow. The workflow plug-in module 270 may further include a reports module 272 configured to generate reports based on the processing of one or more tasks.

Figure 1D:
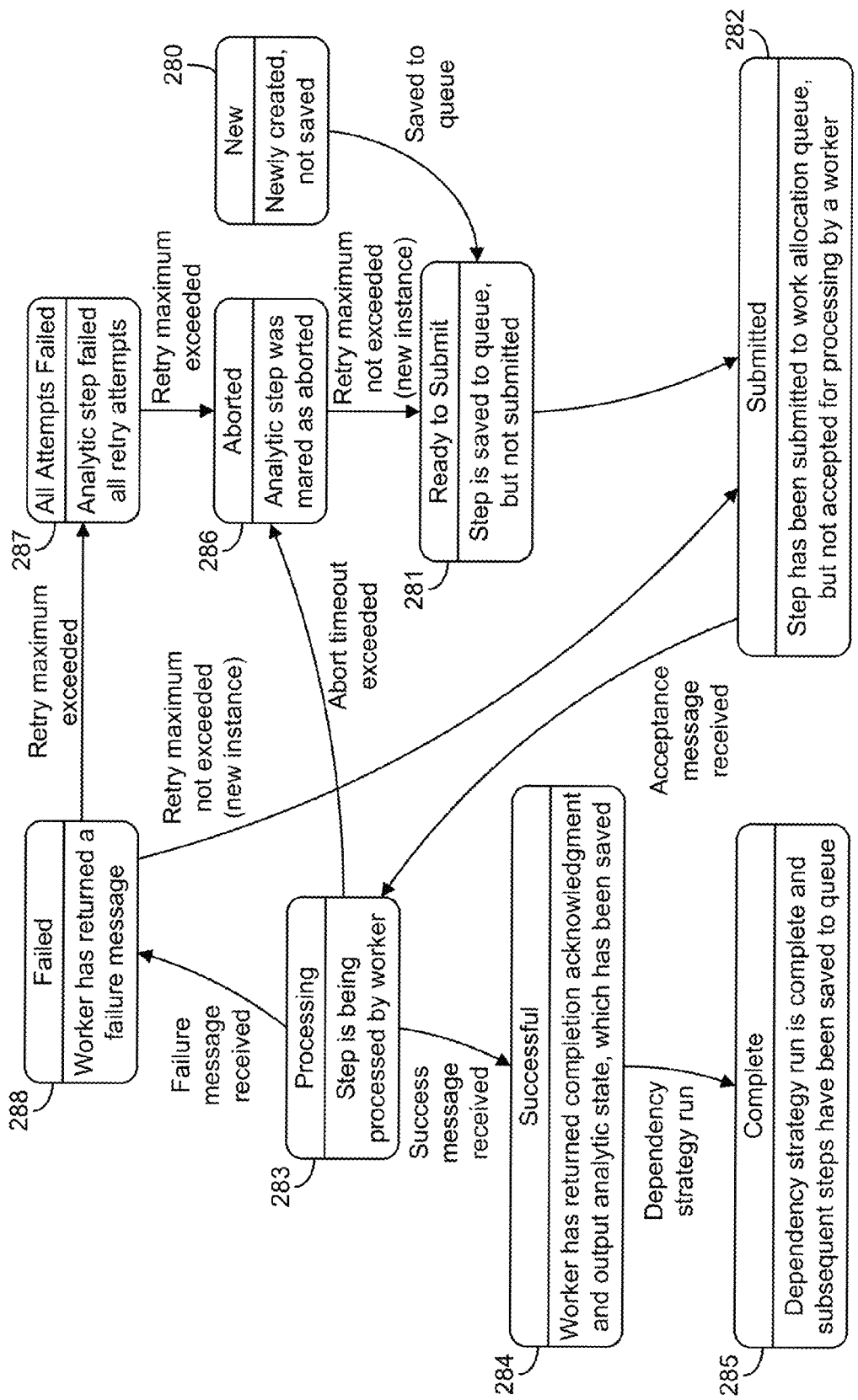
FIG. 1D illustrates a state diagram of scheduling and processing a task in an exemplary embodiment of the computer system for medical analysis and decision support.

Referring now to FIG. 1D, a state diagram illustrating computer system activities is shown according to an exemplary embodiment. The state diagram of FIG. 1D illustrates activities relating to the scheduling and processing of a task in a queue by the computer system.

The process of FIG. 1D begins with a newly created request from a client (step 280). The request is saved to diagnostic queue 265 as described with reference to FIG. 1B. The queue is then in a ready to submit stage (step 281) in which the request is saved but not submitted yet to scheduler 210 for scheduling.

If an analytic worker is available for processing the request, a work allocation message is sent, and the request is provided to scheduler 210. The request is then in a submitted state (step 282). In this state, the request is submitted to work allocation queue 234, but has not yet been accepted for processing by a worker 240. Scheduler 210 may be configured to schedule the task, i.e., to determine when the task should be made available to a worker 240. Once the request is accepted by a worker 240, the request enters a processing state (step 283) in which the request is being processed.

If the request is successfully processed, the request enters a successful state (step 284) in which acknowledgment of the success is indicated. The analytic state resulting from the processing is saved. The request enters a completed state (step 285) when a dependency strategy run is completed, and subsequent steps have been saved to the queue.

If an abort timeout is exceeded (i.e., the task is taking too long to process), the task may enter an aborted state (step 286). The task may be resubmitted for processing. If a retry maximum is exceeded for the task, the task may be marked as "all attempts failed" (step 287). Similarly, if a failure message is received during the processing, the task may enter a failed state (step 288); and the task may be resubmitted to the work allocation queue (step 282) if the retry maximum for the task is not exceeded. If the retry maximum for the task is exceeded, the task is marked as "all attempts failed" (step 287).

Figure 2A:
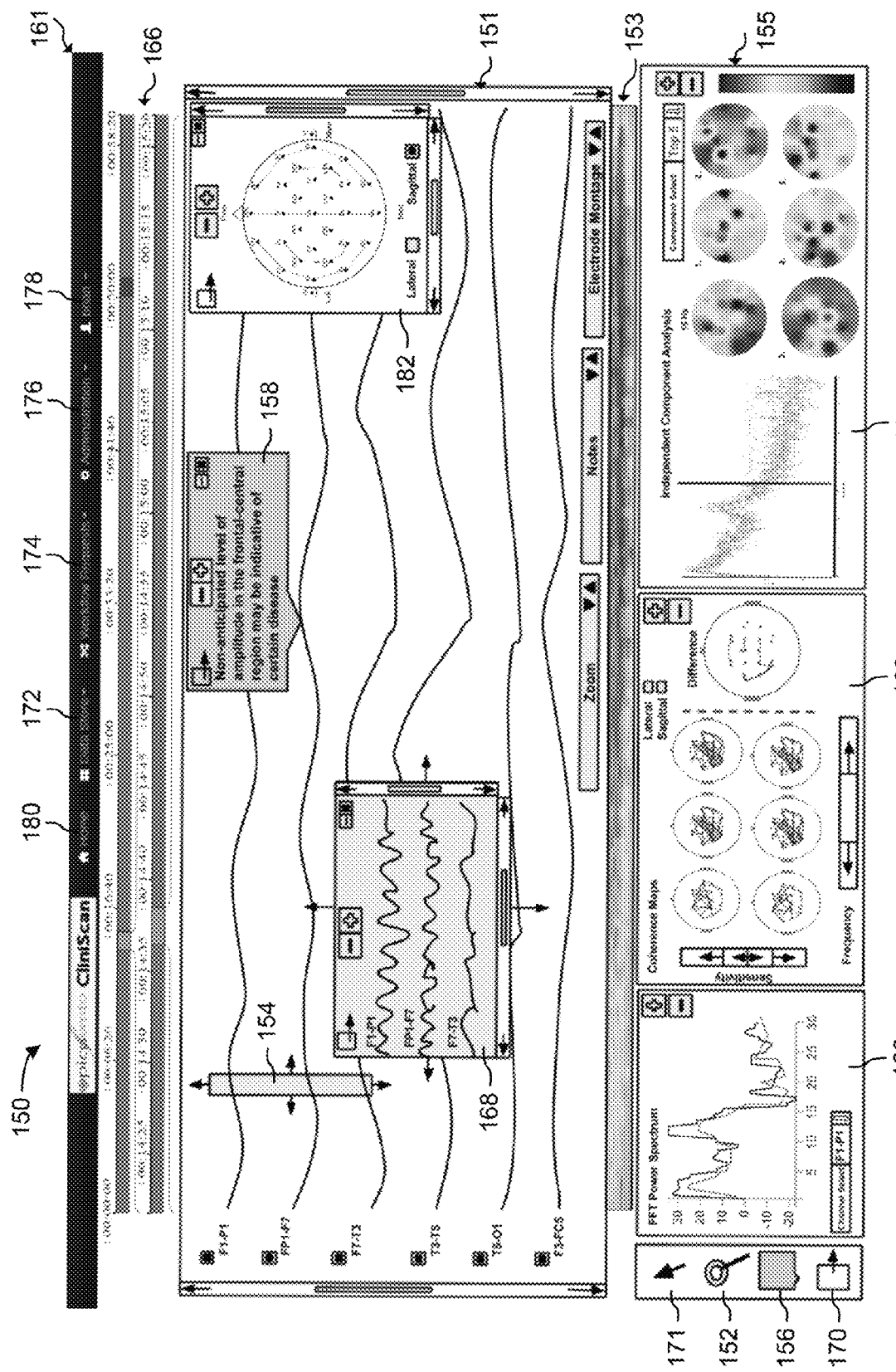
FIG. 2A illustrates a graphical user interface of an EEG decision support system.

Referring now to FIG. 2A, a graphical user interface 150 that may be provided on client device 102 is shown, where EEG data analysis is provided as an example. Graphical user interface 150 shown advantageously provides a comprehensive view of multiple modes of brain analysis.

In some embodiments, user interface 150 includes a menu bar 161 which includes one or more of a home button 180, a data store menu 172, a workflow request menu 174, an administration menu 176 and a profile menu 178. User interface 150 may be generated using processing circuitry and/or according to programming and/or computer code stored in memory. The processing circuitry may also handle user inputs to user interface 150 and perform calculations, make determinations, and/or generate and display output as a result of user inputs. When pressed, home button 180 may take a user to a home screen. In some embodiments, the home screen displays active measurement data. In other embodiments, the home screen may display a summary of information related to one or more of stored data, workflow data, administration and/or settings information, and a user profile or patient profile.

In some embodiments, data store menu 172 displays options related to stored measurement data when a user selects the data store menu 172 icon in menu bar 161. For example, data store menu 172 may include options to save, open, close, switch data sets, or otherwise alter, preserve, or organize measurement data. In some embodiments, data store menu 172 displays options as a drop down menu. In other embodiments, data store menu 172 displays options in a separate window which may overlay all or a portion of the screen displaying measurement data.

In some embodiments, menu bar 161 includes workflow requests menu 174 which displays workflow management options to a user when selected. A user may submit a data set for analysis using workflow requests menu 174. For example, a user may upload or otherwise transfer data and/or tasks to a remote server (for example, analysis server). A workflow request may be or include a set of data accompanied with examination and/or analysis tasks to be completed by an analytic worker. A user may view information about existing workflow requests. For example, a user may retrieve workflow request updates, results, progress information or other status on a submitted workflow item using workflow requests menu 174. A user may also manage workflow requests using workflow requests menu 174. For example, a user may mark a workflow task as completed, submit annotated measurement data, request additional information, prioritize workflow requests, and/or otherwise manipulate workflow requests. In some embodiments, a user may select the type of analysis to be conducted with respect to uploaded data using workflow requests menu 174. For example, a user may request a concussion analysis, brain tumor analysis, or other type of analysis for a set of data. A user may manage multiple workflow requests for the same set of data using workflow request menu 174. In some embodiments, workflow requests menu 174 displays options as a drop down menu. In other embodiments, workflow requests menu 174 displays options in a separate window which may overlay all or a portion of the screen displaying measurement data.

In some embodiments, menu bar 161 includes administration menu 176. Administration menu 176 may allow a user to alter settings of user interface 150. A user may change the default layout of elements of user interface 150 described herein, change default parameters, alter or modify the function of tools within user interface 150, and/or otherwise customize or change user interface 150. In some embodiments, administration menu 176 displays options as a drop down menu. In other embodiments, administration menu 176 displays options in a separate window which may overlay all or a portion of the screen displaying measurement data.

In some embodiments, menu bar 161 further includes profile menu 178. Profile menu 178 may allow a user to view and/or alter information corresponding to a user profile. Profile menu 178 may allow a user to alter information such as a user's availability, status, personal information (for example, name, address, phone number, etc.), or other information unique to a user or which identifies a user in accordance with, but not restricted to, the security standards of the Health Insurance Portability and Accountability Act. In some embodiments, profile menu 178 allows a user to modify defaults, preferences, or other settings related to user interface 150. Profile menu 178 may also allow a user to log into a profile (for example, to load associated preferences, default values, or other settings related to user interface 150), log out of a profile, and/or switch profiles. Profile menu 178 may allow multiple users to access user interface 150 using the same browser and/or computing device.

In other embodiments, profile menu 178 corresponds to a patient profile. A user may alter information regarding a patient associated with a set of measurement data and/or results. For example, a user may alter information such as a patient's name, address, phone number, prognosis, notes, insurance information, next of kin, and/or other information unique to the patient. Profile menu 178 may also allow a user to switch between patients. For example, profile menu 178 may allow a user to save measurement data and/or analysis for a patient, close information about a patient, and/or switch between patient information. In some embodiments, profile menu 178 displays options as a drop down menu. In other embodiments, profile menu 178 displays options in a separate window which may overlay all or a portion of the screen displaying measurement data. In some embodiments, the information displayed and/or altered by profile menu 178 corresponding to a patient is in accordance with the security standards of the Health Insurance Portability and Accountability Act. In other embodiments, the information displayed and/or altered is not restricted to information in accordance with the Health Insurance Portability and Accountability Act.

In some embodiments, menu bar 161 further includes a menu specific to the functions of each modality dynamically loaded into the system, such as EEG decision support modality or MRI/DTI decision support modality.

In some embodiments, visualizers allow analytic data to be displayed on user interface 150 graphically for medical decision support. In some embodiments, the analytic data displayed on user interface 150 includes a navigation bar 166, a wave display window 151, and an analytic toolbox region 155.

In some embodiments where EEG decision support modality is loaded, user interface 150 includes a display of graphs related to electrode activity over time for each electrode attached to a patient (for example, electrode channels). These graphs and/or additional information may be displayed in wave display window 151 or a section of a window making up user interface 150. Each graph may include a label designating the electrode position to which the graph corresponds. Wave display window 151 may include one or more scroll bars for navigating to different electrode graphs and/or navigating to different points in time displayed by the electrode graphs. In some embodiments, only one scroll bar is used to navigate among the graphs corresponding to each channel which are currently displayed. A separate navigation bar 166 may be used to navigate to a different point in time and/or to display a different segment of data corresponding to a particular time. In some embodiments, wave display window 151 is the main window of user interface 150. For example, home button 180 may take a user back to or otherwise display wave display window 151. In further embodiments, wave display window 151 is the first or original window to be displayed to a user.

In some embodiments, navigation bar 166 enables multiple levels of dynamic temporal data browsing. Navigation bar 166 may allow a user to advance the electrode graphs or otherwise cause the electrode graphs to display a different segment of time. In some embodiments, navigation bar 166 includes three bars with the first bar corresponding to days, the second corresponding to hours, and the third corresponding to minutes. In other embodiments, more or less bars are displayed and may correspond to different units of time measurement. For example, a first bar may correspond to hours while a second bar corresponds to minutes. The bars may be delineated with lines or other markings and the corresponding time labeled to ease user navigation of the displayed data by time. In some embodiments, each bar includes a slider. The slider may be configured to correspond in size to the window of time displayed for each electrode graph. The slider may also be positioned along the bar to show the current window of time for which data is displayed. In some embodiments, a user adjusts the window of time for which data is displayed by dragging one or more sliders. In further embodiments, a user may jump to a particular time by clicking, pressing, or otherwise selecting a point along a bar. The bars of navigation bar 166 and/or the corresponding sliders may be adjusted automatically to correspond with the displayed time window when the displayed time window is altered by the zoom function described herein. In cases in which the zoom function is used corresponding to a zoom window 168 and/or a resizable section window 154 described herein, navigation bar 166 may remain unchanged by the zoom function.

Figure 2B:
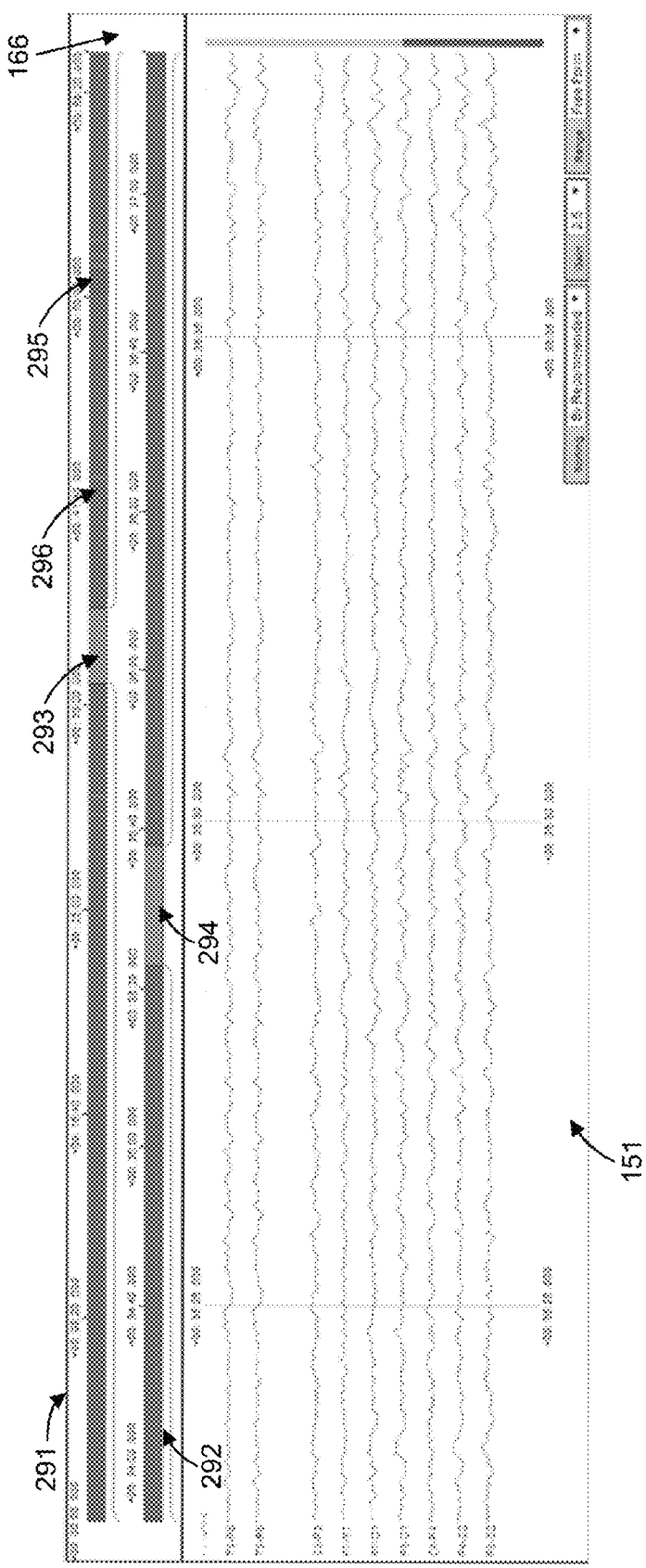
FIG. 2B illustrates a wave display window on a graphical user interface.

In an exemplary embodiment illustrated by FIG. 2B, navigation bar 166 includes two linked bars, a first bar 291 representing the entirety of the EEG data and a second bar 292 displaying a region highlighted by a first slider 293 on first bar 291. A second slider 294 on second bar 292 indicates the region that is being displayed in detail in wave display window 151. On first bar 291 and second bar 292, potentially interesting regions, such as regions 295 and 296, may be highlighted with different colors or other markers.

Referring back to FIG. 2A, in some embodiments, a user may zoom a view of the electrode graphs in wave display window 151 using a zoom button or menu. The zoom button or menu may allow a user to alter the display of user interface 150 by zooming in, zooming out, zooming to fit, zooming to a selection, or other zooming related to the displayed data. In some embodiments, a user may create or otherwise access zoom window 168. For example, a user may select "zoom window" from a zoom dropdown menu or from an option presented in a window. In some embodiments, a zoom icon is included on the window displaying the channel graphs to allow a user to perform zooming functions. Zoom window 168 and a corresponding resizable selection window 154 may be generated and displayed to a user through user interface 150 (for example, by clicking on a zoom icon or otherwise selecting an option to create a zoom window 168). In some embodiments, multiple zoom windows 168 and corresponding resizable selection windows 154 may be shown simultaneously.

Resizable selection window 154 may be resized by a user (for example, by dragging an arrow of the window) such that zoom window 168 displays zoomed in data for the channels and sections of channels encompassed by the area of resizable selection window 154. Additional channels may be added to zoom window 168 when resizable selection window 154 is resized to encompass additional channels. In some embodiments, zoom window 168 includes additional zoom functions which allow further examination of the sections of channels selected by resizable selection window 154. For example, a user may further zoom within a selection of data displayed in zoom window 168 and corresponding to the area within resizable selection window 154. A user may zoom in within zoom window 168 using a zoom in button or icon (for example, a plus sign icon). A user may zoom out within zoom window 168 using a zoom out button or icon (for example, a minus sign icon). Zoom window 168 may include time domain labels which display to a user the time corresponding to the channel graphs being viewed in zoom window 168. In some embodiments, zoom window 168 labels each channel displayed within zoom window 168.

Zoom window 168 may further include navigational scroll bars. The navigational scroll bars may allow a user to change the displayed view of the channel graphs by navigating between channels and/or along the time axis. In some embodiments, zoom window 168 may include a navigation bar corresponding to the segment of time selected by resizable selection window 154. The navigation bar in zoom window 168 may allow a user to navigate the data displayed in zoom window 168 by time as explained above in reference to navigation bar 166. In some embodiments, zoom window 168 is resizable by a user. For example, a user may resize zoom window 168 by dragging on arrows associated with each edge of zoom window 168. In further embodiments, a user may resize zoom window 168 by dragging on a corner and/or edge of zoom window 168.

In some embodiments, zoom window 168 includes icons which allow a user to export, minimize, and/or close zoom window 168. In some embodiments, the export icon (for example, page and arrow) allows a user to have zoom window 168 opened in a new window. The original zoom window 168 may be closed automatically by user interface 150. In other embodiments, the original zoom window 168 may remain. In further embodiments, the export icon allows a user to save the portion of data encompassed by resizable selection window 154 as a separate file, share the portion of data (for example, by e-mail or another program), or otherwise manipulate, remove, and/or copy a segment of data selected by resizable selection window 154.

In some embodiments, user interface 150 includes an electrode-at-a-glance window 182. Electrode-at-a-glance window 182 may display electrode montage information to a user. This information may include a graphical representation showing the location of electrodes and/or labels of electrodes corresponding to the measured channels. Electrode-at-a-glance window 182 may be a miniaturized display formed from an imported electrode montage. Electrode-at-a-glance window 182 may include buttons which allow a user to zoom in and/or zoom out on the electrode montage pictogram, export electrode-at-a-glance information, minimize the window, maximize the window, close the window, and/or otherwise manipulate electrode-at-a-glance window 182. In some embodiments, electrode-at-a-glance window 182 includes one or more scroll bars which allow a user to navigate within the window. Electrode-at-a-glance window 182 may also include buttons which allow a user to select lateral and/or sagittal organization of the electrodes displayed. In some embodiments, a user may select and/or deselect an electrode using electrode-at-a-glance window 182. Selecting an electrode may add a corresponding channel to wave display window 151 (for example, main window or original window). Deselecting an electrode may remove the corresponding channel from wave display window 151. In some embodiments, a user can also add or remove a channel from wave display window 151 by selecting or deselecting the channel on wave display window 151.

Figure 2C:
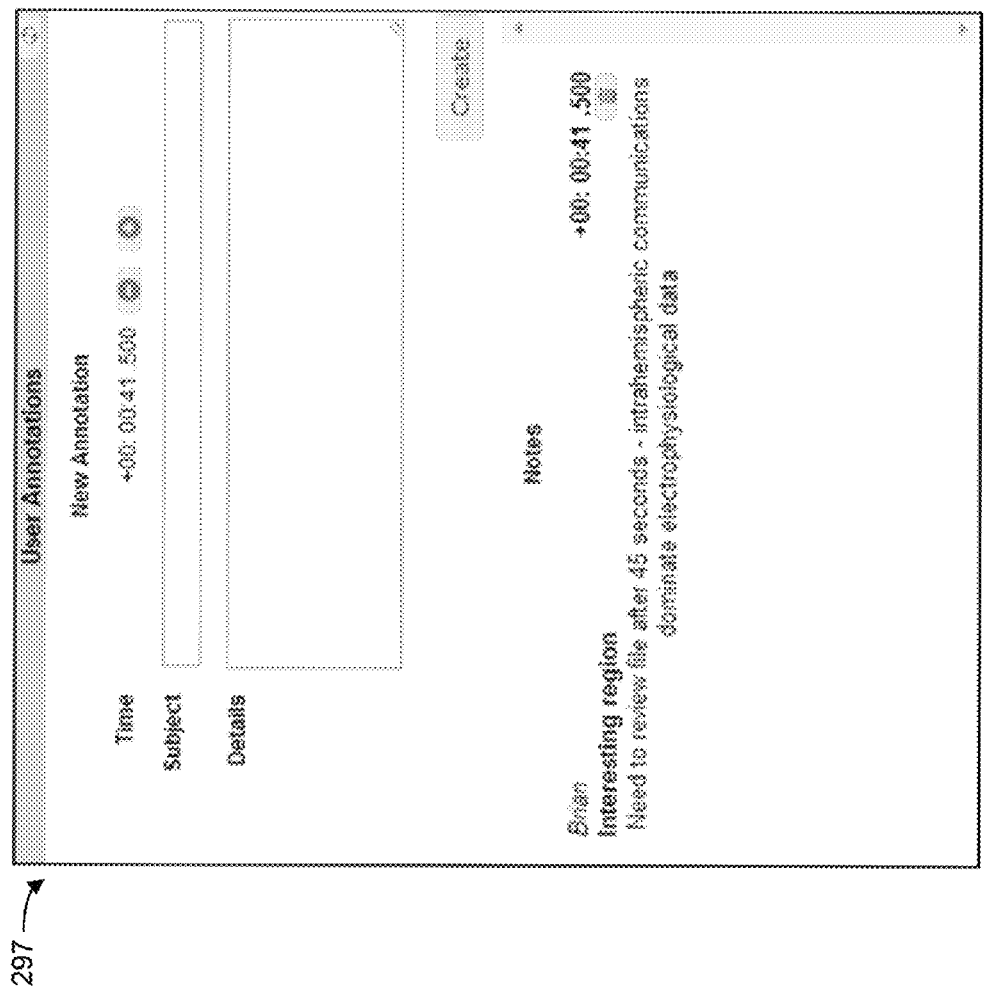
FIG. 2C illustrates an annotation window for in-line annotation on a graphical user interface.

In some embodiments, a user can add in-line annotations 158 to a channel in wave display window 151. An in-line annotation 158 may correspond to a particular point in time on a channel. In some embodiments, clicking on a channel signal creates in-line annotation 158 at the position where the user clicked. In other embodiments, a user creates in-line annotation 158 by selecting in-line annotation button 156 and then selecting the location at which the user wants to create in-line annotation 158. In some embodiments, an annotation window 297 as illustrated by FIG. 2C may be used by the user to enter annotations. In some embodiments, annotation window 297 may overlay a portion of the original window. In some embodiments, annotation window 297 may be displayed in a portion of the user interface 150. For example, annotation window 297 may be displayed next to wave display window 151, and wave display window 151 may be reduced to accommodate window 297. In further embodiments, in-line annotation 158 may be created in any window on user interface 150 using in-line annotation button 156. A user may export in-line annotation 158 using export button 170 and/or an export button on in-line annotation 158. In-line annotations 158 may be exported to a scratch pad, a word processing program, a file, shared, exported to another program, or otherwise exported as described herein with reference to zoom window 168. In some embodiments, in-line annotations 158 include zoom buttons which allow a user to zoom in and/or out on the text of in-line annotation 158. In-line annotations 158 may also include buttons allowing a user to minimize, maximize, close, resize, or otherwise manipulate in-line annotation 158. In some embodiments, in-line annotations 158 are accessible via an annotation list where the user can select or delete any annotation.

In some embodiments, user interface 150 includes magnifying glass tool 152. When a user selects magnifying glass tool 152, a window with a border may be displayed to the user. The user may move and/or resize the window over areas of interest in user interface 150 to view the area at increased magnification of zoom. Advantageously, a user may view an area of interest with greater detail without zooming in an entire window (for example, channel display window). Thus, when a user exits magnifying glass tool 152 (for example, by pressing the icon again, clicking a close icon, or otherwise exiting the window), user interface 150 maintains the original display configuration (for example, level of zoom for each feature).

In some embodiments, user interface 150 includes reports. Reports may be generated from data displayed by user interface 150 or otherwise available. In some embodiments, the reports include one or more of wavelet subband decomposition, FFT power spectrum, coherence maps, independent component analysis (ICA), and density spectral map.

In some embodiments, reports are generated automatically. In other embodiments, reports are generated as requested by a user (for example, by pressing a report button). Reports may be displayed by user interface 150 in the original window corresponding to the report in analytic toolbox region 155. For example, a coherence map report may be displayed in coherence map window 162. In other embodiments, reports are displayed in additional windows, tabs, or other locations. Reports may also be exported to other programs, saved as individual files or series of files, or otherwise stored or transferred outside of user interface 150.

The wavelet subband decomposition provides the user with a tool to examine the frequency subband from any selected EEG channel. Subband decomposition is a form of transformation that breaks a signal into a number of different frequency bands and encodes each one independently. Every signal can be written as a linear combination of wavelets. Wavelets, such as Daubechies 4 wavelets, can be used to break down the chosen channel into different frequency bands. Wavelet transform enables variable window sizes in analyzing different frequency components within a signal. The signal is passed through a series of high pass filters to analyze the high frequencies, and it is passed through a series of low pass filters to analyze the low frequencies. Filtering a signal corresponds to mathematical operation of convolution of the signal with the impulse response of the filter. The decomposition of the signal results in a set of coefficients called wavelet coefficients. In this way, wavelet analysis can be used to break down a given time range of a single channel into the range of known frequency subbands, such as delta (0-4 Hz), theta (4-8 Hz), alpha (8-15 Hz), beta (15-30 Hz) and gamma (30-60 Hz) subbands.

In some embodiments, subbands of a selected channel from one or more channels can be displayed in user interface 150 and/or in a report or exported item. In some embodiments, the subbands of selected channels are displayed to a user in a window overlaying a portion of the original window displaying the channels. In some embodiments, the subbands of selected channels are displayed in a window in analytic toolbox region 155. In other embodiments, subbands are displayed to a user in a separate window, tab, or other display mechanism which does not obscure the original window from which the channels are selected.

Figure 2D:
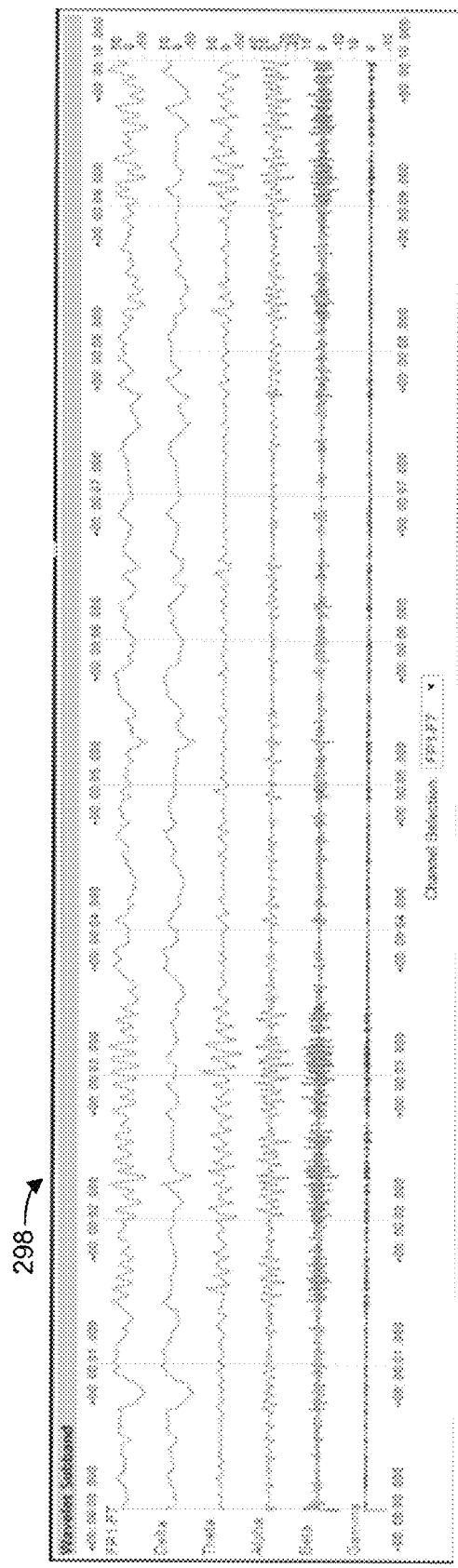
FIG. 2D illustrates wavelet subbands of an EEG channel.

In some embodiments, a user is able to view the subbands of a selected channel and time range as described above. In some embodiments, channels may be selected using a select tool 171. A selected channel may be decomposed into (for example, broken into) a plurality of frequency bands for which EEG information is displayed to a user. For example, a channel may be decomposed into delta, theta, alpha, beta and/or gamma frequency subbands (for example, band waves). FIG. 2D illustrates exemplary wavelet subbands 298 of an EEG channel on user interface 150. This may allow and/or facilitate identification and/or characterization of conditions and/or diseases on particular target frequency bands. For example, a user may use the displayed subbands to analyze only the alpha band for indications of conditions and/or diseases which may be determined from EEG information corresponding to the frequency range of the alpha subband. A user may observe and analyze known conditions and/or diseases from exhibited frequency abnormalities in the subbands using the information presented in user interface 150. A user may also identify a change in variance and/or amplitude in the subbands of the channel. A user may further identify a slowing down of waves which may be related to dementia.

In some embodiments, inputs for generating the subbands include data from a channel corresponding to a selected time range. The data may be raw European data format (EDF) channel data. Outputs may include subbands corresponding to the selected time range including data for subbands for frequency ranges corresponding to delta, theta, alpha, beta and/or gamma frequency subbands. In some embodiments, the subbands have the following frequency ranges in Hz:

| Band Name | Frequency Range (Hz) |
| --- | --- |
| Delta | $0 < f \leq 4$ |
| Theta | $4 < f \leq 8$ |
| Alpha | $8 < f \leq 15$ |
| Beta | $15 < f \leq 30$ |
| Gamma | $30 < f \leq 60$ |

In other embodiments, subbands may have different frequency ranges. Channels may be broken down into more or less subbands. In some embodiments, a user may change the number of subbands and/or the frequency ranges for each subband. The above listed frequency subbands and frequency ranges may be the default values.

In some embodiments, channels may be displayed in an EEG channel summary report page. In one embodiment, EEG channel summary report is displayed in the channel display window. In some embodiments, the EEG channel summary report page is a separate window, tab, or exported item. In other embodiments, the EEG channel summary page is a window displayed along with the other windows described herein with respect to FIG. 2A.

In some embodiments, a user may select a channel and a time range (for example, using select tool 171). User interface 150 may then display the corresponding subbands of the channel for the selected time range adjacent to the selected channel. In some embodiments, this function is performed automatically when a channel is selected. In other embodiments, a user selects a channel and selects an option (for example, by pushing a button) to display the subbands. In further embodiments, subbands may be displayed for selected channels displayed by user interface 150 and not just channels which are part of an EEG summary report. For example, subbands may be displayed as described above when a user selects a channel in an EEG variance report (for example, seizure detection) page. In some embodiments, each subband is displayed in a separate frame including an x-axis displaying time and a y-axis displaying electrical signal potential difference. The electrical signal potential difference may be expressed in microvolts in EEG physical space. In some embodiments, user interface 150 includes a graphical user interface element which allows a user to request a FFT power spectrum for a selected portion of one or more subbands.

Referring again to FIG. 2A, in some embodiments, user interface 150 includes an FFT power spectrum window 160. FFT power spectrum is a graph of power versus frequency. It provides relative and absolute measures of the expression of frequencies of an EEG signal. FFT power spectrum window 160 may display the frequency distribution of waves in a signal for selected channels. This may show how prevalent certain frequencies are over other frequencies. In some embodiments, the FFT power spectrum is indicative of the type of cortical or subcortical, rhythmic or unexpected behavior. FFT power spectrum window 160 may display information for one or multiple channels from all or a selection of channels. In some embodiments, select tool 171 is used to select the channels and/or portions of channels for which information is displayed in FFT power spectrum window 160. As channels and/or portions of channels are selected for display in FFT power spectrum window 160, the axes may adjust automatically to the ranges of the data to be displayed. Graphs may be color coded with a different color corresponding to each channel displayed. In some embodiments, graphs are labeled with the corresponding channel.

The FFT power spectrum may be used as an analysis method for diagnosis and/or clinical correlation. An EEG technologist and/or attending physician may access FFT power spectrum data through user interface 150 to determine the most prevalent frequencies present in the selected channels from a biopotential. This information may be used to form a clinical diagnosis by analyzing the FFT power spectrums present in FFT power spectrum window 160.

In some embodiments, FFT power spectrum window 160 may be minimized, closed, exported, and/or resized as described with reference to zoom window 168. FFT power spectrum window 160 may include a dropdown menu which allows a user to select a particular channel. When selected, the graph corresponding to the selected channel may be highlighted so as to allow a user to focus on a particular channel. In some embodiments, a user can select multiple channels to highlight. FFT power spectrum window 160 may also include buttons or icons which allow a user to zoom the graphs displayed in FFT power spectrum window 160 (for example, a plus sign icon and a minus sign icon).

FFT power spectrum window 160 and select tool 171 may allow a user to select part of a channel signal to show a corresponding FFT power spectrum graph so as to scrutinize at which absolute and relative levels certain frequencies of interest are exhibited. A user may also view multiple FFT power spectrums of different wave portions selected from a single or multiple wave channels for comparison. In some embodiments, FFT graphs are shown independently from each other and/or next to the wave being analyzed (for example, to the right or left side, above or below, or otherwise located near or adjacent to the corresponding wave channel). In other embodiments, multiple graphs may be displayed in a single window as separate graphs (for example, displayed separately in FFT power spectrum window 160). In further embodiments, multiple graphs may be displayed overlapping one another on a single set of axes. This may allow a user to more easily compare data.

In some embodiments, FFT power spectrum graphs may be exported to or otherwise shown in channel summary reports, wavelet subband reports, and/or ICA reports. As described in detail below, in ICA decomposition, each component may have independent signals from which the power of a frequency can be calculated. Components may be individual electrodes or electrode pairs. Related ICA reports may be generated from or to accompany an FFT power spectrum report (for example, FFT power spectrum exported data). For example, FFT power spectrum reports may include an accompanying heat map graph shown side by side with FFT power spectrum data. The heat map may allow a user to see the level at which a frequency of interest is present in signals from some or all electrodes. In some embodiments, the FFT power spectrum may be shown from ICA channels. An accompanying heat map may show how the frequency of interest is or will be distributed over a two dimensional space and/or a three dimensional space.

In some embodiments, the above described reports, an FFT power spectrum report, FFT power spectrum data and/or analysis, and/or other information related to the FFT power spectrum are exported and/or generated using an export icon in FFT power spectrum window 160. In other embodiments, the above reports and information may be exported and/or generated when a user selects export button 170. In some embodiments, FFT power spectrum window 160 is exported when a user selects export button 170 if it is an active window. In other embodiments, a user selects the information to be exported after pressing export icon 170. The same may apply to other windows and/or information included in user interface 150. Similarly, export button 170 may save, transfer, move, share, or otherwise manipulate information, results, and/or data included in user interface 150.

Still referring to FIG. 2A, user interface 150 includes a coherence maps window 162 in some embodiments. Coherence quantitatively measures the linear dependency between two distant brain regions expressed by their EEG activities. The coherence of a signal pair is a correlation coefficient (squared); it measures the phase consistency between pairs of signals in each frequency band. Scalp recorded EEG coherence is a large-scale measure, which depicts dynamic functional interactions between electrode signals. High coherence between EEG signals recorded at different sites of the scalp indicates an increased functional interplay between the underlying neuronal networks. Coherence at a frequency f for two signals x and y is derived from the cross-power spectrum and the two corresponding auto-spectra. Coherence values lie within a range from 0 to 1, whereby 0 means that both signals are not correlated at the corresponding frequency; 1 means frequency components of the signals are fully correlated with constant phase shifts, although they may show differences in amplitude.

In some embodiments, coherence maps window 162 may include two main panels. One panel may show coherence values for six different frequency ranges. The other panel may show the difference between coherence maps. In some embodiments, the two panels are labeled and/or separated visually (for example, with a dashed line). Coherence maps window 162 may include a sensitivity bar for adjusting a separator marker and/or a range of values to be displayed. The sensitivity bar may be manipulated as a slider and/or a particular position or value selected. In some embodiments, coherence maps window 162 includes a frequency selector which adjusts the range of frequencies for which coherence is calculated. The range may be displayed to a user and updated as a user makes adjustments using the frequency selector. The frequency selector may be manipulated as a slider and/or particular values are selected. In some embodiments, the range of frequencies may be adjusted by a user dragging an end of the selected band to the left or right to increase or decrease the frequencies encompassed in the range. In some embodiments, a user may select lateral and/or sagittal connections. For example, a user may select the connections using check boxes included in coherence maps window 162.

In some embodiments, coherence maps window 162 may be minimized, closed, exported, and/or resized as described with reference to zoom window 168. Coherence maps window 162 and/or associated data, information, and/or analysis may be exported as described above with reference to FFT power spectrum window 160. Coherence map window 162 may also be zoomed and/or navigated using icons, buttons, and/or scroll bars as described above in reference to other features of user interface 150.

A clinician, technician, physician and/or other user may desire to view the coherence values between electrodes on unipolar montage or between pairs of electrodes on a bipolar montage. Coherence maps window 162 may display this information. This may allow a user to get to a more precise or sharper diagnosis based on the interactions, interrelationships, and/or interdependencies between cortical areas over a particular frequency domain. In some embodiments, the coherence analysis is processed on all channels for a selected time range. In other embodiments, the coherence analysis is processed on selected channels. Channels and/or time ranges may be selected using select tool 171. In other embodiments, channels and/or time ranges may be input by a user using fields, buttons, sliders, and/or other graphical user interface elements. In some embodiments, the coherence analysis is performed automatically and offered to the user via a prompt. The user may be prompted after the user has finished browsing through the channel data. In other embodiments, the coherence analysis is performed only upon a user input requesting the analysis.

A coherence report may be generated as part of an export action as described above. A coherence report may also be generated and displayed in coherence map window 162. In some embodiments, a user selects the time range for the coherence report. A default time range may be calculated and presented to a user or used in the absence of a user time range selection. In some embodiments, the default time range for the initial display is determined by the range in which the most abnormal signals occur (for example, seizure detection range). A user may change the time range. For example, a user may drag a time bar (for example, vertical time bar). The coherence report may automatically update based on the changed time range and be displayed to a user.

In some embodiments, the coherence report includes a two dimensional and/or three dimensional coherence map for each subband. The coherence maps may show highlighted coherence values that are in a range around a particular threshold (for example, a baseline). In some embodiments, the coherence report includes a coherence value table which allows a user to view the coherence values between any two electrodes and/or between pairs of electrodes. This may be illustrated in a two dimensional and/or three dimensional coherence map. Coherence reports may include a plurality of coherence maps.

In some embodiments, the coherence map shows highlighted coherence values that are in a range around a particular threshold (for example, a baseline), which are displayed as connections between electrodes (for example, a unipolar montage) and/or connections between electrode pairs (for example, a bipolar montage). Coherence maps may be grouped and/or displayed in subbands or by subbands. In some embodiments, each subband coherence map includes one subband coherence map for the entire subband frequency range and/or a list or series of coherence maps corresponding to broken down frequency ranges of the subband. The subband names and/or labels may also be displayed. In some embodiments, a fixed 2 Hz coherence map size is used. This results in the generation of a coherence map for every 2 Hz segment of a subband.

In some embodiments, the threshold (for example, baseline) and coherence value range for highlighting coherence values is adjustable. A user may select the threshold and/or range (for example, using sliders, buttons, fields, or other graphical user interface elements). The coherence maps may update automatically. The default threshold for initial displays may be a random value, median value, average value, or other value of coherence. The default value ranges may be random values (for example, 0.2 below and above the default threshold). In other embodiments the default range value is fixed. In some embodiments, defaults may be customized or otherwise defined by a user (for example, through administration menu 176).

The combination of connection line color and weight displayed in coherence maps may indicate which range the coherence value is in (for example, coherence values ranges of 0.0-0.5, 0.5-1.0, etc.). Coherence value ranges may be defined by a user. In some embodiments, a red line is used for connections that have coherence values above the threshold and blue lines for connections which have coherence values below the threshold. The coherence value range indication lines (for example, blue or red lines) displayed on user interface 150 (for example, in coherence maps windows 162 and/or a coherence report) may be actual coherence values (for example, 0.00-1.00) and/or converted coherence values (for example, −0.10-0.10). The line thickness of the connection line may correspond to the coherence value. In some embodiments, the weight of the connection line is greater for higher coherence values (for example, the higher the coherence value, the thicker the connection line).

In some embodiments, a user can select or deselect coherence illustrations (show or hide connection lines) between electrodes or electrode pairs. A user may also restore default coherence illustrations for the current threshold and coherence value range. For example, a user may toggle coherence illustrations on or off using a corresponding button. In some embodiments, a user may set a default (for example, to show or to not show coherence illustrations). A user may enlarge a coherence map to see details of the coherence map. Advantageously, this may make it easier to analyze a coherence map containing a large number of connections. In some embodiments, a user may enlarge a view of a coherence map using zoom icons and/or scroll bars. In other embodiments, a user views an enlarged coherence map in a separate window when a user clicks on a coherence map, double clicks on a coherence map, selects an enlarge button, or otherwise provides a user input to enlarge a coherence map. In some embodiments, a user selects the connection templates which are used in the display of coherence maps. Connection templates may be sagittal connections, lateral connections, and/or a combination of sagittal and lateral connections. The default may be to display both sagittal and lateral connections. In some embodiments, this default may be set by a user.

Figure 3:
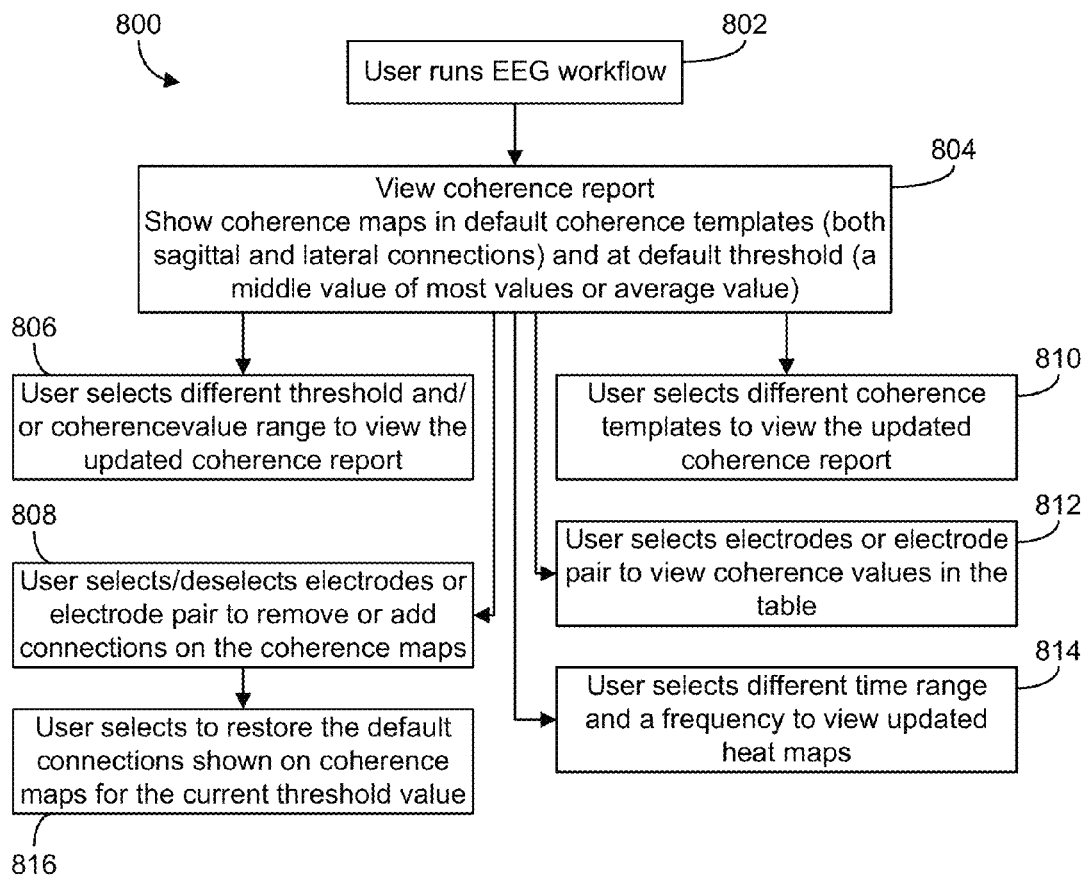
FIG. 3 illustrates a workflow for calculating coherences of an EEG signal.

In some embodiments, a plurality of connection templates may be chosen to show in coherence maps. If an electrode is present in a coherence map (for example, called for by a coherence map template) but data is not available corresponding to that electrode, the coherence may be calculated between the next closest neighbor electrode in the order. In other embodiments, different calculation techniques may be used to deal with missing electrode data. For example, electrodes surrounding the missing electrodes may be averaged and/or interpolated. The calculation techniques which are used are not limited to the exemplary techniques of averaging and/or interpolation. The same techniques may be used to handle missing electrode pairs. For example, a connection template may be:

Sagittal Oriented Connections:
i) Left Hemisphere
1) F1-FC1-C1-CP1-P1
2) FP1-AF3-F3-FC3-C3-CP3-P3-PO3-O1
3) F5-FC5-O5-CP5-P5
4) AF7-F7-FT7-T7-TP7-P7-PO7
5) F9-FT9-T9-TP9-P9
ii) Right Hemisphere
1) F2-FC2-C2-CP2-P2
2) FP2-AF4-F4-FC4-C4-CP4-P4-PO4-O2
3) F6-FC6-C6-CP6-P6
4) AF8-F8-FT8-T8-TP8-P8-PO8
5) F10-FT10-T10-TP10-P10
iii) Cross-Sectional Lines—Mid-Sagittal
1) Nz-Fpz-AFz-FCz-Cz-CPz-Pz-POz-Oz-Iz
Laterally Oriented Connections:
i) Front
1) Fp1-Fpz-Fp2
2) AF7-AF3-AFz-AF4-AF8
3) F9-F7-F5-F3-F1-Fz-F2-F4-F6-F8-F10
4) FT9-FT7-FC5-FC3-FC1-FCz-FC2-FC4-FC6-FC8-FT10
ii) Back
1) TP9-TP7-CP5-CP3-CP1-CPZ-CP2-CP4-CP6-TP8-TP10
2) P9-P7-P5-P3-P1-Pz-P2-P4-P6-P8-P10
3) PO7-PO3-POz-PO4-PO8
iii) Cross-Sectional Lines—Mid-Lateral
1) T9-T7-05-C3-C1-Cz-C2-C4-C6-T8-T10
All Connections Referring now to FIG. 3, a flowchart 800 illustrates a workflow map for a user initiated coherence calculation based on an EEG signal according to one embodiment. A user runs or otherwise initiates an EEG workflow (802). A user may run a workflow through workflow request menu 174 of user interface 150. A coherence report which may include coherence maps is then displayed to a user in user interface 150 which a user may view (804). The coherence report may be generated using default values for the parameters used in generating the coherence report. In some embodiments, a user may modify the default values prior to submitting the workflow request using administration menu 176. In other embodiments, a user may modify the default values while submitting a workflow request through workflow request menu 174 and/or after the report has been received using user interface 150. For example, a user may select a difference threshold and/or coherence range value, and the coherence report may update (806). As described herein, the coherence report may update automatically when the user selects new values. In other embodiments, the user may submit the new values as a workflow request which results in an updated coherence report. A user may also select or deselect electrodes or electrode pairs in the coherence map (808). The coherence maps may then be updated as just described (for example, automatically or manually). In some embodiments, a user may restore the default selection of electrodes or electrode pairs (816). This may be an optional step. In some embodiments, the coherence report (for example, in coherence maps window 162) includes a button which allows a user to restore the default display.

In some embodiments, a user may also select a different coherence template to change the coherence maps displayed (810). In some embodiments, a user may import templates for use in this step. In some embodiments, coherence maps may be recalculated when a user switches templates to account for missing electrode data. A user may also select an electrode or electrode pair to view associated coherence values in an accompanying coherence table (812). Additionally, a user may select a different time range and/or frequency which results in an updated heat map (814). As explained above, the selection may be made with select tool 171. In some embodiments, other user interface 150 elements such as fields, sliders, and/or buttons may be used to select different time range and/or frequency values. In some embodiments, all the steps of flowchart 800 are voluntary. In further embodiments, a user may take additional actions not illustrated in the depicted embodiment of flowchart 800. For example, a user may zoom in and/or out, select subbands to view associated coherence maps, etc.

In some embodiments, the inputs used to generate a coherence map include one or more of a waveform file corresponding to the selected time range or a portion of a waveform file corresponding to the selected time range and/or coherence map frequency size. The default coherence map frequency size may be 2 Hz. The default coherence map frequency size may be adjustable by a user. Each subband may output a coherence map for every 2 Hz of the subband.

In some embodiments, the output of generating a coherence map includes a series of coherence maps for each segment of a subband (for example, every 2 Hz). Each subband coherence map includes a subband object. The subband object may include the subband name and the frequency range of the subband. Each subband coherence map set may also include a coherence map of the full subband and/or a series of coherence maps with each coherence map corresponding to a frequency range forming a subset of the frequency range of the entire subband. For example, the frequency ranges corresponding to the series of coherence maps for each subband may be as follows:

| Band Name | Frequency Range of Subband (Hz) | Frequency Ranges of Each Coherence Map of the Subband (Hz) |
| --- | --- | --- |
| Delta | $0 < f \leq 4$ | $0 < f \leq 2; 2 < f \leq 4$ |
| Theta | $4 < f \leq 8$ | $4 < f \leq 6; 6 < f \leq 8$ |
| Alpha | $8 < f \leq 15$ | $8 < f \leq 10; 10 < f \leq 12; 12 < f \leq 15$ |
| Beta | $15 < f \leq 30$ | $15 < f \leq 17; 17 < f \leq 19; 19 < f \leq 21; 21 < f \leq 23; 23 < f \leq 25; 25 < f \leq 27; 27 < f \leq 30$ |
| Gamma | $30 < f \leq 60$ | $30 < f \leq 32; 32 < f \leq 34; 34 < f \leq 36; \ldots 54 < f \leq 56; 56 < f \leq 58; 58 < f \leq 60$ |

Referring now back to FIG. 2A, in some embodiments, user interface 150 includes one or more ICA windows 164. ICA is a computational method for separating a multivariate signal into additive subcomponents by assuming that the subcomponents are non-Gaussian signals and that they are statistically independent from each other. ICA is a special case of blind source separation.

An ICA algorithm, for example, the FastICA algorithm, can be implemented as follows. A data matrix X is considered to be a linear combination of non-Gaussian (independent) components, i.e., X=A×S, where columns of S contain the independent components and A is a linear mixing matrix. ICA attempts to "unmix" the data by estimating an unmixing matrix W such that W×X=S. Under this generative model, the measured signals X tend to be more Gaussian than the source components in S due to the Central Limit Theorem. In order to extract the independent components/sources, an unmixing matrix W that maximizes the non-gaussianity of the sources is searched. In FastICA, non-gaussianity is measured using approximations to neg-entropy (J) which are more robust than Kurtosis-based measures.

First, the data are centered by subtracting the mean of each column of data matrix X. The data matrix is then "whitened" by projecting the data onto its principal component directions i.e. X→X×K where K is a pre-whitening matrix. The number of components can be specified by the user, the upper limit of which is the number of channels.

The ICA algorithm then estimates a matrix W such that W×X=S. W is chosen to maximize the neg-entropy approximation under the constraints that W is an orthonormal matrix. This constraint ensures that the estimated components are uncorrelated. The algorithm may be based on a fixed-point iteration scheme to maximize the neg-entropy. In the absence of a generative model for the data, the algorithm can be used to find the projection pursuit directions. Projection pursuit is a technique for finding interesting directions in multidimensional data sets. Interesting directions are those which show the least Gaussian distribution. These projections are useful for visualizing the data sets and in density estimation and regression.

ICA when applied to EEG signal processing breaks down the EEG signal recorded by electrodes into independent components. The objective is to isolate and localize the sources of electrical activity within a specified frequency domain. The projected component data has the same size as the original data, has the same basis (i.e. each row is a single electrode, as in the original data), and is scaled in the original data units (for example, microvolt). The effect of each detected projected component on each electrode can be expressed in power terms and shown through heat maps. Heat maps may be displayed with head representations, and the power of a component is assumed to decay with a radial linear gradient drawn out from its center. For monopolar montages, the center of the effect of the component on a particular electrode is the position of that electrode, while for bipolar montages, the midpoint between two electrodes is the center of the detected component.

In some embodiments, the effect of each of top 5 most powerful projected components, with the effect of one projected component per heat map, and the effect of all projected components, in a composite heat map, can be shown. The other projected components may be available via toggle buttons.

In some embodiments, ICA window 164 may show the results of one or more ICA algorithms. In some embodiments, ICA breaks down a wave recording for the electrode into independent components. Each component may be data (for example, power) corresponding to a single electrode or electrode pair. The number of components may vary but is limited by the number of channels. For example, a user may determine the number of components and/or particular components to be used in ICA. ICA may isolate and/or localize the sources of electrical activity within a specified frequency domain. ICA may result in one or more graphs which fall into three types. A graph may be generated illustrating FFT power spectrums for the independent components (for example, electrodes). This may show the relative and absolute frequency distribution for each component. A graph may be generated showing a component heat map. The heat map may be two dimensional or three dimensional. In some embodiments, the heat map shows the weight of each independent component on every electrode at a particular frequency. A graph may also be generated showing a composite component heat map. The composite component heat map may be two or three dimensional and show, at a particular frequency, the influence of all components on all electrodes.

One or more of these graphs and/or additional information may be displayed in ICA window 164. ICA window 164 may include a display of the power spectrum of detected components with a selected frequency or frequency range. The display may be a heat map. ICA may also include heat maps of detected components. For example, ICA window 164 may display the top five components (for example, the components with the highest readings). In some embodiments, these heat maps are labeled 1-5. They may additionally be labeled to identify the components and/or additional information such as the frequency or frequency range. In some embodiments, the display may be customized. A user may determine what is displayed. For example, a user may display the bottom five components. In some embodiments, a user may adjust the number of components for which the influence is shown.

In some embodiments, ICA window 164 includes a heat map scale bar. The heat map scale bar may include a color legend with values indicating a spectrum from highest component power values to lowest component power values and the associated color used in the heat maps. The lowest and highest power at each electrode for all of the top 5 components are used to dictate the lower and higher ends of the numeric scale on the color scale bar. In other words, for each component, the amplitudes of scalp maps give the size of the component projections at a particular frequency during a chosen time region. In some embodiments, the spectrum is first blended as alpha masks over each other, and then converted into a color mapping with Red as the power representing the highest power and Blue representing the lowest power. ICA window 164 may also include buttons, icons, scroll bars, and/or other features described herein with reference to other windows which allow a user to zoom, scroll, navigate, minimize, maximize, close, resize, export, or otherwise manipulate ICA window 164 and/or the data displayed therein.

In some embodiments, a clinician or other user may review the results of the ICA performed on the channel data through ICA window 164. Advantageously, ICA window 164 allows a user to view a power spectrum (for example, power vs. frequency) and a component heat map so that the user can see how the powers of separated sources have affected the EEG recording in each electrode. The user may also visualize the approximate location of the sources. Some heat maps may also be pre-calculated depending on automatic default values or user defined values.

In some embodiments, the ICA analysis is processed on all channels for the selected time range. The time range may be selected with select tool 171. In other embodiments, a user may select the time range using other elements of user interface 150 such as fields, buttons, sliders, or other elements. In some embodiments, the ICA is done automatically and a user is prompted to view the results after the user has finished browsing through the channel data. In other embodiments, a user is prompted to view the ICA results at a different time. In further embodiments, a user manually selects to perform the ICA analysis and/or view the results. The default time range may be calculated and presented to a user or used in the absence of a user time range selection. In some embodiments, the default time range for the initial display is determined by the range in which the most abnormal signals occur (for example, seizure detection range). A user may change the time range. For example, a user may drag a time bar (for example, vertical time bar). The ICA report may automatically update based on the changed time range and be displayed to a user.

In some embodiments, the ICA report includes an FFT power spectrum for each component. FFT power spectrums for each component may be displayed in separate frames with the x-axis corresponding to frequency and the y-axis corresponding to power in squared microvolts. The y-axis may be logarithmically scaled. In other embodiments, the FFT power spectrums of multiple components are illustrated in the same frame. A user may select a frequency range for which the FFT power spectrums of the components are shown. The default range may be 0 to 30 Hz. In some embodiments, a user may select a different default range. A user may select the frequency by dragging a slider along the x-axis of the power spectrum to illustrate the most powerful components at that frequency. The heat maps may automatically update based on the frequency.

As described above, in some embodiments, the ICA report includes a composite component heat map in two or three dimensions. The composite component heat map shows the relative influence of all components at the same frequency. The frequency for which composite component heat map data is displayed may be the same frequency for which the other heat maps (for example, individual component heat maps) are displaying data. In some embodiments, selecting a frequency in the composite component heat map automatically updates the component heat maps to display for the same frequency. In further embodiments, selecting a frequency in the component heat maps automatically updates the composite component heat map to display for the same frequency. A user may select a frequency in the composite component heat map in the same way as selecting a frequency in the component heat maps (for example, using a slider).

In some embodiments, both the composite component heat maps and the component heat maps are displayed above a power spectrum which dynamically updates to display data for the currently selected frequency. In other embodiments, the heat maps and power spectrum may be oriented in other configurations. In some embodiments, the default frequency for which information is displayed is 12 Hz. The default frequency may be other values. In some embodiments, a user may select the default frequency.

In some embodiments, the input data used to generate and/or display the above discussed data includes all channel data of the selected time range (for example, the waveform file). Inputs may also include the selected frequency for which the heat maps will display data. In some embodiments, ICA outputs (for example, the ICA report and/or ICA window 164) include a series of components with one FFT power spectrum corresponding to each component and an associated frequency range. FFT power spectrums for corresponding components may be generated and/or displayed for multiple frequencies or frequency ranges. For example, a user may select a particular frequency range (for example, 15-30 Hz) for which FFT power spectrums are displayed for each component. A user may select the frequency range through user interface 150. In some embodiments, a user selects the frequency range using select tool 171. In other embodiments, other graphical user interface elements are used. For example, the frequency range may be selected using fields, buttons, scroll bars, or other elements. User interface 150 may display FFT power spectrums for a default frequency range. The default may be modified by a user in some embodiments.

In some embodiments, the ICA outputs include heat maps for five components which correspond to the highest measured powers at a specific frequency. The specific frequency may be a default value (for example, 12 Hz). In some embodiments, a user may select the frequency (for example, 16 Hz) through user interface 150. For example, a user may select the frequency using select tool 171. In other embodiments, other graphical user interface elements are used, such as sliders, buttons, fields, etc. In one embodiment, the values illustrated on the five component heat maps are not the power values (for example, the power values displayed on the FFT power spectrum). The values illustrated with the five component heat maps may be calculated separately. In some embodiments, the values displayed on the five heat maps are calculated by determining the influence of each component on every channel (for example, the relative influence of power of independent sources on the power of electrode outputs). The heat maps may show the power at each electrode or electrode pair relative to other electrodes or pairs. The calculation may include projecting each component on every channel. The power of each channel resulting from the projection (for example, weighted powers) may be shown on the heat maps.

In other embodiments, different calculation techniques may be used to illustrate the influence of power of independent sources on power of electrode outputs. In some embodiments, a different number of heat maps may be displayed. For example, user interface 150 may display five component heat maps as a default setting. Additionally, displaying component heat maps for the five components with the highest power (for example, relative power or power influence) may be a default setting. These default settings may be changed by a user through user interface 150. In some embodiments, a user may choose what is displayed or otherwise alter the display for component heat maps using a drop down menu. For example, a user may select to display the components with the highest powers, the lowest powers, etc. In some embodiments, component heat maps corresponding to particular components are viewable when selected from the drop down box by a user. Advantageously, a user may select components of interest and view associated heat maps to see an illustration of the effect of power measured for the selected component on other components. In other embodiments, the component heat maps display absolute power or other non-relative information for the components. In further embodiments, a user may choose or otherwise determine what information is presented in the form of component heat maps.

In certain embodiments, the ICA outputs also include one or more composite component heat maps. The composite heat map may correspond to a particular frequency (for example, 16 Hz). In some embodiments, the composite component heat map displays the sum of the weighted powers of each component for each signal channel. The composite component heat map may be a composite of each individual component heat map. In some embodiments, the composite component heat map is a composite of all component heat maps. In other embodiments, the composite component heat map is a composite of only the component heat maps displayed to the user (for example, the five component heat maps corresponding to the five components with the highest powers).

Figure 4:
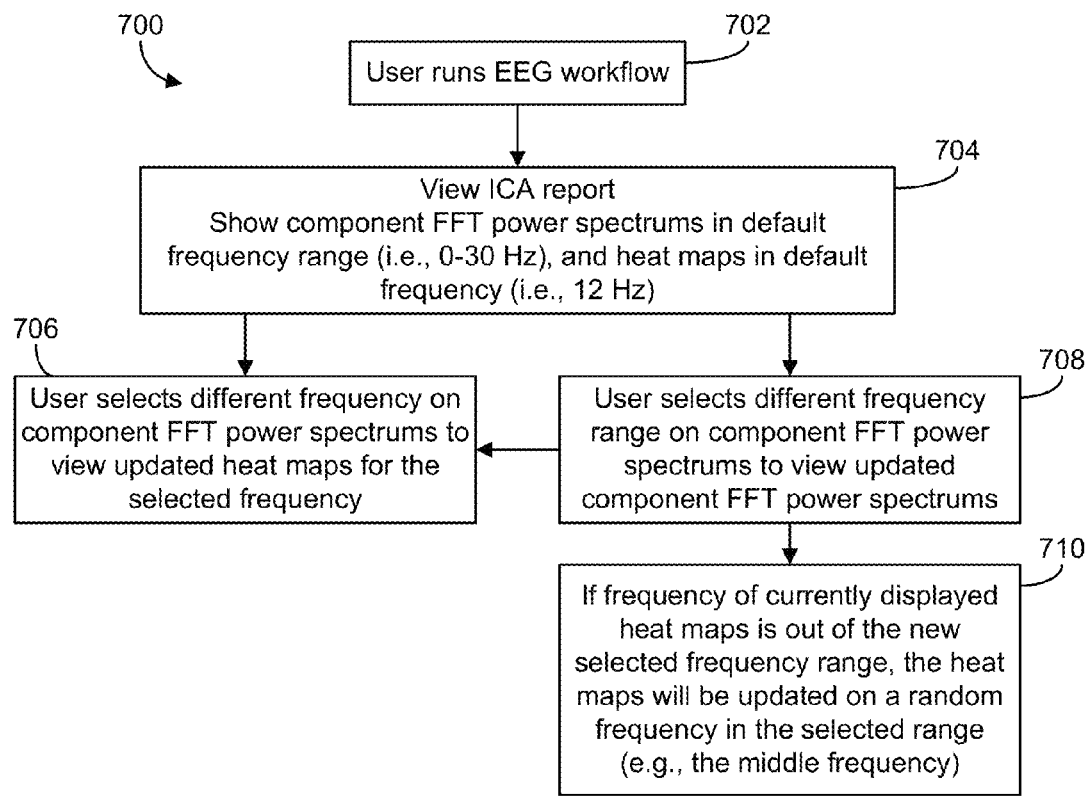
FIG. 4 illustrates a user workflow flowchart for independent component analysis of an EEG signal.

Referring now to FIG. 4, a user workflow flowchart 700 for ICA of EEG signals is illustrated according to an exemplary embodiment. A user may run or otherwise initiate an EEG workflow (702). For example, a user may run a workflow using workflow request menu 174 of user interface 150. An ICA report may be generated and displayed to a user for viewing (704) in response to the workflow request. In some embodiments, the ICA report is generated using default values. The default frequency range may be 0-30 Hz for the component FFT power spectrums. The default frequency for heat maps (component heat maps and/or a composite component heat map) may be 12 Hz. As explained above, a user can change the default values in some embodiments. For example, a user may change the default values through user interface 150 when making a workflow request using workflow request menu 174, through administration menu 176, or otherwise. In some embodiments, a user may select a different frequency range for which to view component FFT power spectrums (708). In some embodiments, the FFT power spectrums automatically update upon this selection and are displayed to the user in user interface 150. As explained above, the frequency may be selected using one or more graphical user interface components including select tool 171, fields, buttons, sliders, and/or other elements.

In some embodiments, if the frequency for which the heat maps are being displayed falls outside the newly selected frequency range for component FFT power spectrums, the heat maps will automatically update and display information for a frequency within the new frequency range (710). In some embodiments, the new frequency for the heat maps is selected randomly or pseudo randomly from within the range of frequencies selected by the user for the FFT power spectrums. In other embodiments, the frequency may be selected by other means. For example, user interface 150 may prompt a user (for example, in a window or pop-up) to select a new frequency for the heat maps within the frequency range chosen for the FFT power spectrums; the frequency may be automatically selected as the frequency with the highest power value in the frequency range; the frequency value may be automatically selected as the frequency with the lowest power value in the frequency range; or the frequency value may otherwise be selected based on the frequency range of the FFT power spectrums. In some embodiments, the heat maps may cease displaying information until a user selects a new frequency. In further embodiments, a user may determine a default action to be taken in this scenario.

After the ICA report is displayed and/or after the user selects a frequency range for the component FFT power spectrums, a user may select a new frequency on a component power spectrum for which to view associated heat maps (706). The heat maps may be component heat maps and/or composite component heat maps as explained above. In some embodiments, the heat maps are updated automatically following the selection of a frequency. A user may select a different frequency on a component FFT power spectrum for which to view associated heat maps using select tool 171. For example, a user may select a frequency and/or point of interest on an FFT power spectrum and the associated frequency will be used to update the heat maps. In further embodiments, a user selects the frequency using one or more of fields, buttons, sliders, and/or other elements of user interface 150.

In some embodiments, all the steps of flowchart 700 are voluntary. In further embodiments, a user may take additional actions not illustrated in the depicted embodiment of flowchart 700. For example, a user may zoom in and/or out, select specific components to view associated heat maps, etc.

In some embodiments, user interface 150 also includes density spectral maps. Density spectral array (DSA) provides the ability to visualize frequency and power distribution of EEG signals over time. In a spectral density map, the X-axis may be time with increments corresponding to the length of a sliding time window; the Y-axis may be frequency scaled from 0 to 60 Hz. Each individual value at an x-y position is the power for the frequency and time converted to a color map. The result is a graphical representation of the dominance of particular frequencies over others at different time. For instance, in some embodiments, color spectrum may use red to illustrate high prevalence and blue to illustrate low prevalence. Therefore, at a glance, a user may learn which frequencies are dominant.

Figure 2E:
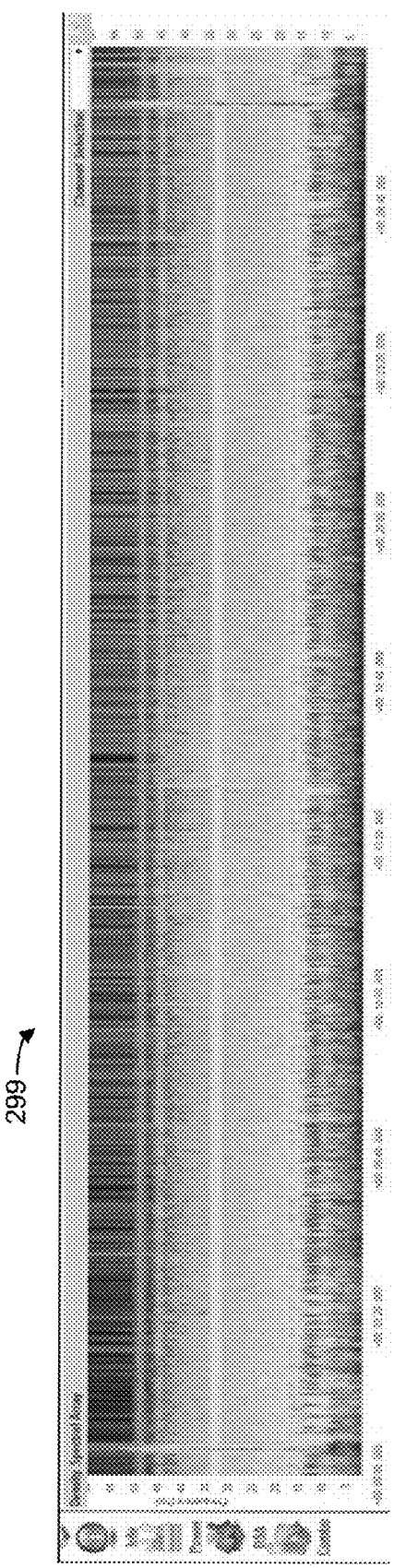
FIG. 2E illustrates a density spectral map of an EEG signal.

Referring back to FIG. 2A, in some embodiments, the density spectral map can be provided in two forms. A first density spectral map 153 may be generated for the entirety of the wave signal and displayed in a miniature form between wave display window 151 and analytic toolbox region 155. A second density spectral map 299 illustrated by FIG. 2E may be accessible via the analytic toolbox on the bottom left side of the user interface 150, for example, using a "DSA" button. In other embodiments, the density spectral map may be displayed elsewhere in user interface 150 or in a separate window. In some embodiments, the density spectral map may be minimized, closed, exported, and/or resized as described with reference to zoom window 168. The density spectral map may also be zoomed and/or navigated using icons, buttons, and/or scroll bars as described above in reference to other features of user interface 150. The density spectral map and/or associated data, information, and/or analysis may be exported as described above with reference to FFT power spectrum window 160. For example, in some embodiments, the density spectral map and information may be exported and/or generated when a user selects export button 170. In some embodiments, the density spectral map is exported when a user selects export button 170 if it is an active window. In other embodiments, a user selects the density spectral map after pressing export icon 170.

Figure 2F:
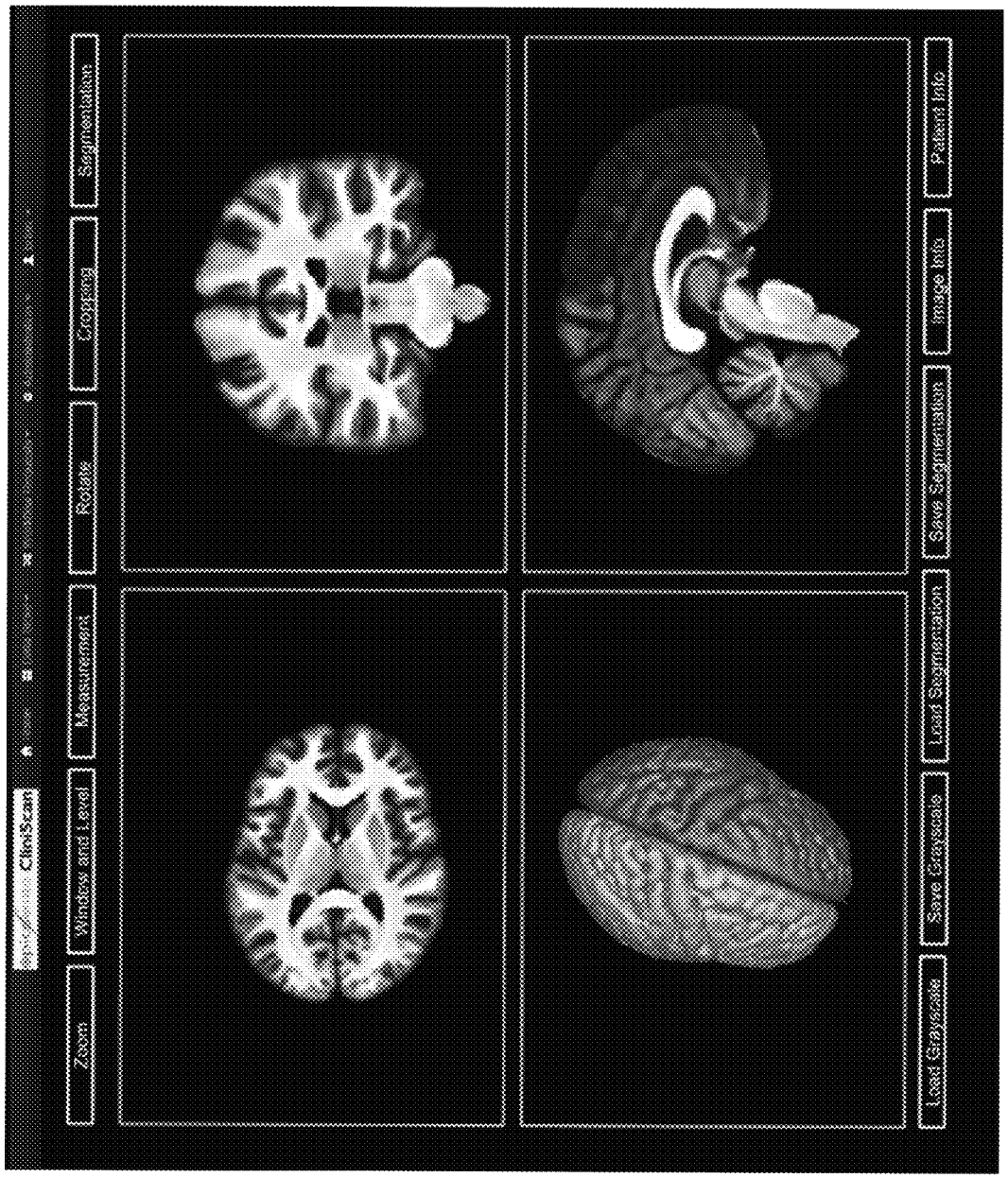
FIG. 2F illustrates an interface for MRI manipulation and analysis.

Referring now to FIG. 2F, a user interface for MRI manipulation and display is shown, according to an exemplary embodiment. As previously described, the user can upload MRI test data for storage and processing in a cloud environment. Thus, even if the user is not on a workstation class computer, the user can experience a high degree of MRI viewing and manipulation features. A workflow can exist in the analysis server that conducts image quality assurance processing to test the quality of the MRI data. This processing can be intended to avoid a garbage-in/garbage-out scenario. The downstream processes that utilize MRI data for analysis and/or joining with EEG data or other types of inputs may be configured to rely on high quality image data. The quality of the data may be tested using a histogram analysis or another type of statistical processing relative to a reference or threshold. The quality process conducted by a workflow may be automated to detect images with a relatively high noise and remove the high noise images from an image stack. In other embodiments, the process can tag images as high noise and suggest to the user (for example, via the user interface) the removal of the high noise image from the image stack.

Referring still to FIG. 2F, the graphical user interface is configured to provide a user interface element (for example, button) for launching a windowing and leveling feature. The windowing and leveling feature can provide an input pixel value intensity vs. display color intensity graph. The user can interact with (for example, via clicks, drags, swipes, etc.) the graph to adjust the level and window of the image. The windowing and leveling tool may include control points along the curve of the input pixel value intensity vs. display color intensity graph to facilitate the adjustment of parameters.

The windowing and leveling feature may be one of a subset of filtering features the system can provide for interacting with the MRI data. In addition to the filtering provided by the windowing and leveling feature, the graphic user interface (GUI) may include a tool for allowing users to define (for example, via a scripting code, via manual entry of numerical filter parameters, etc.) custom filters. The custom filters may be applied to provide custom thresholding or for image transformations.

The MRI user interface of FIG. 2F may further include a color map selection and adjustment feature. The color map feature may provide for the selection of color maps between pre-stored varieties (for example, gray scale, color map for bone imaging, conventional RGB, fire-red scale maps for PET and SPECT precision from binary to 64-bit pictures). Color maps may automatically be chosen (for example, by a workflow of the system) based on image content or imaging modality. Custom color maps may be uploaded by the user.

The MRI user interface of FIG. 2F may further provide image transformation tools. The image transformation tools, in an exemplary embodiment, may be provided and executed by matrix manipulation. The user can adjust or utilize a pre-stored transformation matrix or can use a GUI tool to input a custom transformation matrix. Pre-stored transformation matrix tools may provide for rotation, scaling, shearing, inversion, reflection, or translation. As shown in FIG. 2F, certain transformations may receive their own buttons in the user interface (for example, rotation).

As further shown in the image of FIG. 2F, the GUI can include a button for launching a cropping tool. Two dimensional and three dimensional images may be cropped from the user interface and the resultant images can be saved.

In various exemplary embodiments, the MRI tool can process data input or file formats including digital imaging and communication in medicine (DICOM) of three dimension (structural imaging), diffusion tensor image (DTI), fMRI, four dimension, longitudinal studies, radiotherapy formats, or other past, present or future MRI data formats. In an exemplary embodiment, the input data is subject to one or more image conversion steps. For example, the image can be normalized, converted to a standardized format for processing by further workflows and analytic processes, compressed, and/or packaged for more rapid or efficient retrieval or processing.

Referring still to the MRI tool of FIG. 2F, measurement tools can be provided for user evaluation of the images. The user can be provided with position markers. Upon placement of such markers, tools including customizable user-placed rulers for distance, customizable user-placed curved lines for length estimates, a tool for judging surface area of a closed traced or selected object, or a tool for judging volume can be provided. Traced or object selection tools can be assisted or automatically completed using edge detection segmentation tools. The object selection tool may allow for user input of object vertices that are used for volume calculation of the object.

Referring still to FIG. 2F, the MRI tool can further provide registration and alignment tools for the MRI image sets. The registration and alignment tools can generally assist with the process of geometrically aligning the set of MRI images onto a coordinate system for further processing. The alignment method can utilize the Tailarach coordinate system that defines the maximum dimensions of the brain as three planes of space: x (anterior commissure-posterior commissure (AC-PC) line), y (vertical commissure anterior (VCA) line) and z (midline). Affine transformations such as linear transformations, rotation, scaling and other co-linear translations may be provided. These transformations may be determined by maximizing a similarity metric (for example, mutual information) via optimization techniques, such as gradient descent. Non-affine translations such as basic radial functions, large deformation models, physical continuum models and other non-co-linear transformations can also be provided according to various exemplary embodiments. One or more algorithms including Optical Flow, Demon, Diffeomorphic Demon, Log Based Diffeomorphic Demon, Random Walk Based Diffeomorphic, and/or additional algorithms may be used alone or in combination as non-rigid registration methods. In some embodiments, multiple two dimensional and/or three dimensional panels may be available to view various MRI image sets, with cross-hairs on each panel. Using registration and segmentation, cross-hairs across all panels can be linked so that they may refer to the same anatomical position.

Referring still to FIG. 2F, the drawing and segmentation tools for interacting with the MRI images can include surface and volume extraction, generation and calculation tools. Such tools can be used for manual segmentation of the MRI images and can provide a suite of tools for manual segmentation. These tools can include threshold filters, bubbles, edge detection algorithms, or isosurface creation tools (including tessellation-based and/or smoothed surface based). The edge detection tools can include types such as sobel, canny or magic wand tools. The sobel tool can provide a discrete differentiation operator used to calculate a gradient of the image intensity. The canny tool can be used to detect a wide range of edges via a multi-stage algorithm. The magic wand tool can be used to allow the user to make quick selections (for example, simple point and click mouse moves). The edge detection tool can allow for thresholding and/or range selection so that the user can adjust the tool for the quality or other characteristics of the input image. Segmentation tools can be imported and stored in a variety of ways including binary, raw, Neuroimaging Informatics Technology Initiative (NIFTI), or DICOM. As noted above with respect to other data types, one or more workflows may be provided for processing or converting the imported data. An imported file may be compressed, for example, to provide for better file transfer performance. In an exemplary embodiment, the MRI tool is compatible for other radiotherapy formats and tools. Plans for image-guided radiation therapy (RT) can be output and can include dosage calculations, programming of beam strength, compatibility with DICOM-RT, DICOM format for RT, or other plan types. Image support may further include RT image, RT dose, radiotherapy structure set (RTSTRUCT), RT plan, and RT treatment record.

In some embodiments, the diffusion of water molecules in white matter (WM) and/or fiber tracts are used to map the degree of anisotropy and/or the local fiber direction structure as axonal membranes and myelin sheaths act as barriers to the motion of water molecules. Water molecules may be barred from moving in directions not parallel to the orientation of local fiber (for example, axonal membranes and myelin sheaths). Using one or more of MRI diffusion weighted images (DWI) and diffusion tensor images (DTI), a voxel map (three dimensional map using discrete volumes) may be created illustrating WM physical interconnectivity and interconnectivity to other cranial structures. In some embodiments, DTI data is integrated with DWI data to create the voxel map of WM.

In some embodiments, fiber reconstruction techniques and/or fiber tracking through diffusion tensor deflection are used in creating a fiber-voxel map corresponding to WM (for example, showing the path of greatest water molecule diffusion). As explained above, this information may be useful as the path of greatest water molecule diffusion follows the local fiber direction as axonal membranes and/or myelin sheaths inhibit non-parallel water molecule diffusion. Lines in the voxel map may be propagated to show the pathway of greatest water molecule diffusion. The line may begin propagating from one or more seed points. In some embodiments, a user selects a seed point. For example, a user may select a seed point by clicking on a voxel or a location within a voxel of the voxel map of WM. The line will propagate and be added to the fiber-voxel map of WM in the direction of maximum diffusion within the voxel. When the line reaches a boundary between the current voxel and an adjacent voxel, the line may change direction to follow the path of maximum diffusion in the adjacent voxel. In some embodiments, the change in direction is abrupt depending on the path of greatest diffusion in the adjacent voxel. The line may be propagated using a tracking algorithm. The tracking algorithm may be repeated using a plurality of seed points.

In some embodiments, the tracking algorithm and/or voxel map generation process does not produce a visual representation of a tract unless the tract is longer than a minimum value. In some embodiments, the minimum value is fixed and/or a default value. In other embodiments, a user may specify a minimum value and/or alter a value from its default setting. In some embodiments, a threshold anisotropy for a voxel must also be met in order for a tract to be shown (for example, for the line to be propagated in the voxel). In some embodiments, the threshold anisotropy value is set by a user. There may be a default value. The choice of the position, shape, and/or density of seed points and/or the threshold anisotropy value may be determined based on the types of cranial structures of interest. In some embodiments, a user determines these parameters. In other embodiments, a user specifies a structure or structures of interest, and one or more of the parameters are determined without further user input (for example, by an algorithm). In some embodiments, a uniform, low density of seed points may be generated for an overview of the entire brain. Advantageously, a low density of seed points may decrease computational time used in tracking (for example, propagating the line according to an algorithm which determines the path of greatest diffusion) and/or in rendering an image or display (for example, a voxel map of the WM). In some embodiments, a user may be able to determine the number of seed points. Thus, a user may balance computational requirements and accuracy and/or precision.

Figure 2G:
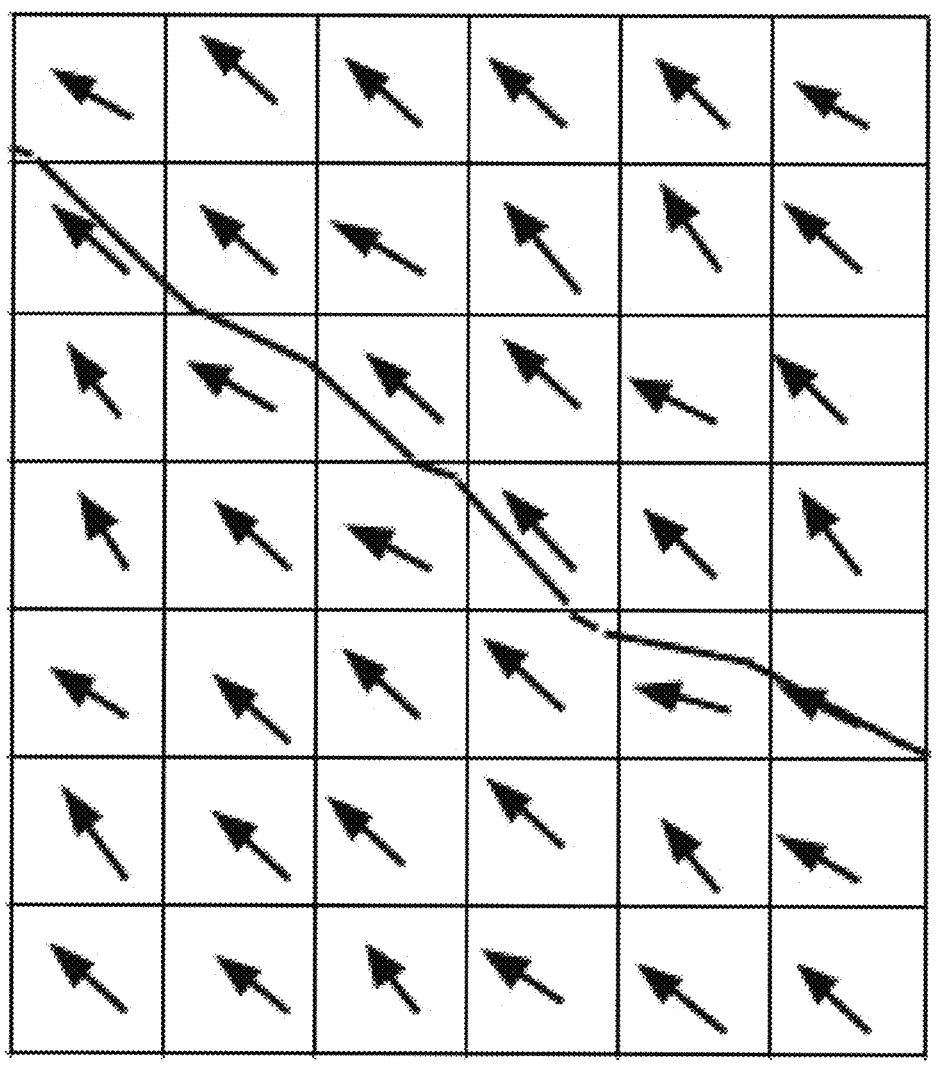
FIG. 2G illustrates a method of parallel fiber assignment with continuous fiber tracking.

Referring now to FIG. 2G, a parallel fiber assignment with a continuous tracking (named PAFACT here) approach (for example, algorithm) to fiber tracking is illustrated according to one embodiment. In some embodiments, PAFACT is used to create a voxel map and/or other visual representation of WM (for example, interconnectivity and/or interconnectivity of WM to other cranial structures). The result may be a three dimensional image or a two dimensional image. PAFACT may track based on a continuous coordinate system instead of using discrete voxels as described above. Advantageously, this may increase accuracy and/or precision. The system may provide a further advantage by limiting the increase in computation time and/or required local computing resources by making use of massively parallel cloud computing. A discrete voxel based grid system may be substituted for a continuous eigenvector based system.

In some embodiments, the fiber tracking starts in the center of a voxel or other location where the fractional anisotropy value (FA) is greater than a threshold value. The threshold may be a fixed or default value, or may be specified and/or modified by a user. The fiber tracking may then move along the orientation of a principal eigenvector related to the local fiber orientation. In some embodiments (for example, those using massively parallel cloud computing), each seed starts on a different thread, and at the end of the mapping, intercepting fibers are merged. In some embodiments, propagation of the line used for displaying to the user and/or representative of the path of analysis is terminated in a region of low anisotropy. In some embodiments, line propagation resumes in areas of anisotropy exceeding the threshold value. In other embodiments, line propagation may continue from other seed points, but once a line is terminated, it is no longer propagated. The process of line propagation and/or termination may be repeated until relative anisotropy falls below a threshold value. Relative anisotropy falling below the threshold value may indicate that the tract is no longer in WM and/or that the uncertainty in direction of maximum diffusion is large. The threshold value may be fixed, a default, input by a user, or a user selectable default. In some embodiments, the source of the threshold may be another source such as the result of an algorithm, imported, etc.

In some embodiments, PAFACT and/or the generation of the image corresponding to WM may include smoothing. Noise error may accumulate as propagations become longer. Smoothing may reduce the effect of noise using smoothing and/or interpolation techniques. In some embodiments, PAFACT also includes branching. When using the branching approach, all pixels in the brain are used as seed pixels rather than using one or more discrete pixels (for example, a pixel of interest) as seed pixels. Tracking may be initiated from all pixels within the brain with tracking results that penetrate the pixel of interest retained. In certain embodiments, PAFACT uses a fast marching technique to minimize the energy required to travel from an arbitrary point to the seed pixel. A fast marching algorithm may determine a path which minimizes the cost incurred in travelling from an arbitrary point to the seed pixel. For example, the path may be determined by following the gradient of the steepest step. Other techniques available to or included in PAFACT may include simulated annealing. Simulated annealing may be used to connect two points using minimal energy cost. If two selected points are not connected by the real tract, the energy to force a connection between them is large even for the energy minimized path.

In some embodiments, the techniques and/or tools described above may be used for registration and/or alignment. For example, using MRI methods such as DWI, DTI, apparent diffusion coefficient (ADC), fractional anisotropy (FA), and/or tractography a structural scan may be completed. Constraints to the DTI data may be applied. Following registration, constraints may be applied such that DTI data overlaps with WM only. In some embodiments, a tensor application can convert DWI data to DTI data. The steps may include inputting tensor information, applying the tensor application and reviewing the tensor application output. The output may include graphical and/or numerical components.

In some embodiments, parametric maps may be generated using one or more of the above described techniques and/or tools. Parametric maps may include apparent diffusion coefficient and/or mean diffusivity maps. Parametric maps may also include fractional anisotropy maps. Parametric maps may include and/or be directional colored maps which illustrate tensor orientations. Threshold values may also be labeled and/or illustrated. In some embodiments, parametric maps may be two dimensional on three orthogonal planes. In further embodiments, parametric maps are three dimensional rotatable maps with or without links to two dimensional views. A user may view a two dimensional view by clicking on a portion of the three dimensional map which is linked to a two dimensional view. This may be visually indicated to a user.

In some embodiments, multiple types of tractography are used. Line propagation algorithms may be used. In some embodiments, global energy minimization may be used in addition to or in place of line propagation algorithms. Tractography may include parameter selection such as the algorithm used, the number and/or location of seeds, step size, stopping criteria, and/or other parameters related to tractography. A directional color map may be generated for viewing tensor orientations. Thresholds may also be labeled and/or displayed. In some embodiments, a two dimensional image may be produced using these techniques (for example, tractography). In further embodiments, the image is three dimensional and may include links to two dimensional views.

In some embodiments, a comparison to normative databases, normative values, and/or atlases is made. For example, normative values may be accessed for ADC and/or FA. In some embodiments, tracts and/or linked areas exhibiting abnormal metrics are automatically detected. In further embodiments, WM fibers are automatically labeled. Segmentation of WM tracts and/or probabilistic mapping may be used. Labeled WM bundles may include: corticospinal tract (CST); inferior longitudinal fasciculus (ILF); uncinated fasciculus (UNC); anterior or thalamic radiation (ATR); cingulum-cingulate gyms (supracallosal) bundle (CCG); cingulum-angular (infracallosal) bundle (CAB); superior longitudinal fasciculus parietal bundle (SLFP); superior longitudinal fasciculus-temporal bundle (SLFT); corpus callosum-forceps major (FMAJ); and/or corpus callosum-forceps minor (FMIN). In other embodiments, additional and/or different bundles are labeled.

Figure 5:
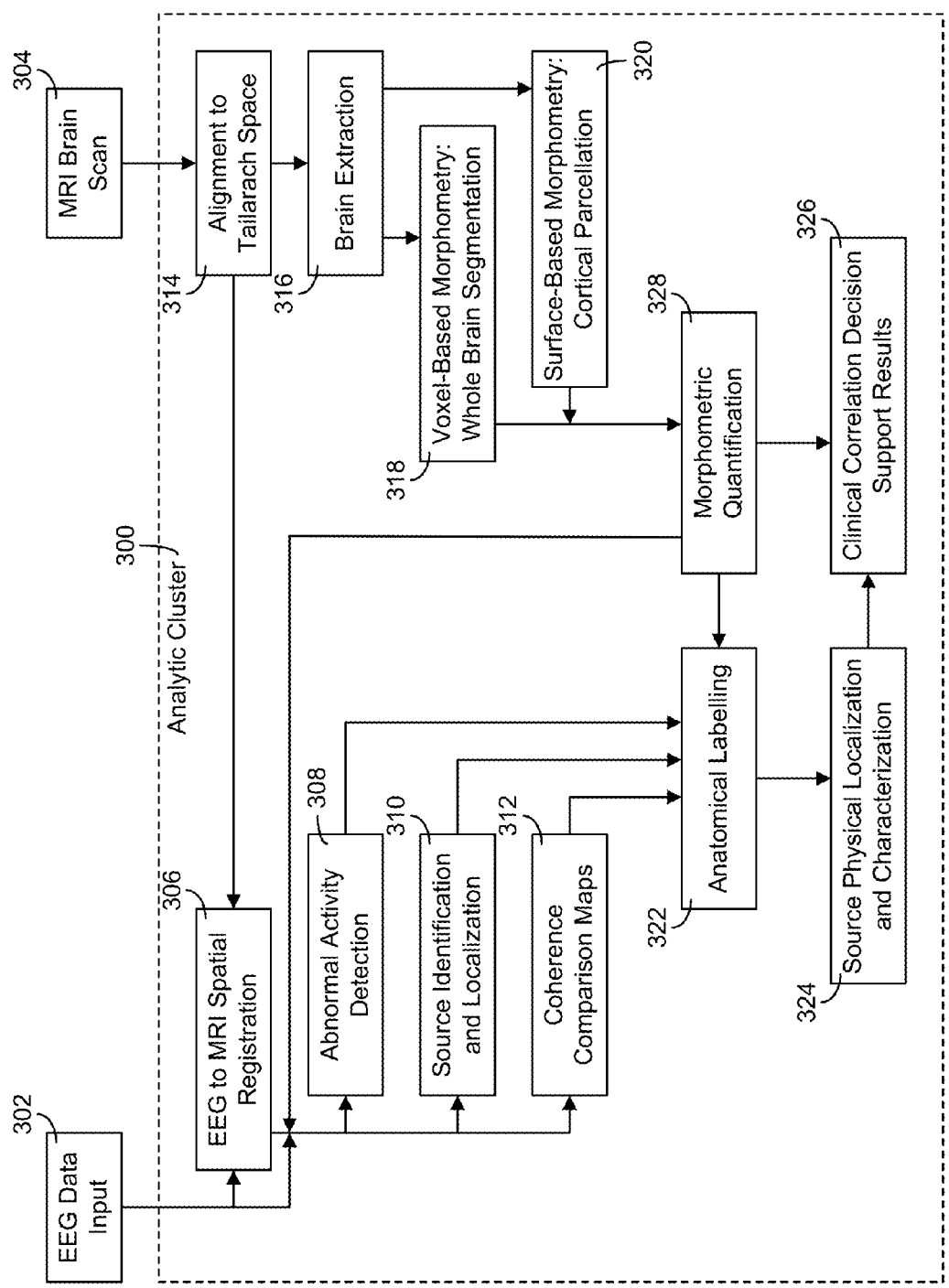
FIG. 5 illustrates a flow diagram for parallel processing EEG data input and MRI brain scan input in an analytic cluster.

Referring now to FIG. 5, a flow diagram of a system and process for utilizing EEG data input 302 and MRI brain scan input 304 is shown, according to an exemplary embodiment. These inputs may correspond to the inputs shown in and discussed with reference to FIG. 1A. The analytic cluster 300 may refer to the analysis server 104, its analytic workers, and the remote storage system 110. As described with reference to Figures above, these three components operate together to provide the server side processing environment of the present application. In an exemplary embodiment, the blocks of FIG. 5 represent processing tasks to be completed using analytic workers that can be working in parallel with other analytic workers. The MRI input represented as MRI brain scan 304 may take the form of a whole brain in T1-, T2-, or Proton Density-Weighted images (for example, about 25 MB of input data) while the output of certain steps (for example, step 328) may be a detailed segmentation output (for example, about 400 MB of output data).

The process depicted in FIG. 5 advantageously combines results of EEG with brain segmentation from MRI. The process can automatically associate the location of a source (for example, electrode, high energy event detected by a system of electrodes, problem area detected by EEG, etc.) with an MRI-labeled brain region or multiple brain regions. Whole brain segmentation from structural MRI can parcel the brain into over 37 different regions and automatically detect morphometric abnormalities. Conventionally, no dual EEG and MRI brain segmentation processing is available in the same set of commercial user interfaces. Not only do the systems and methods of the present application provide a platform for ingesting, processing and providing EEG and MRI brain segmentation results in the same set of interfaces, but also provide the ability to combine their data. This combination can advantageously provide for more accurate EEG analysis, for example. Given that each region of the brain is associated with its own functionality and interconnectivity within the central nervous system (CNS), localization of a source of electrical activity from EEG signals can advantageously allow for a closer diagnostic behind the detected electrical activity in the brain. Conventional methods without cortical parcellation and subcortical segmentation, which would include merely overlaying the display of localization of a source from EEG processing on an MRI without detailed processing, does not provide good association of anatomical structure with electrical source.

Referring now to the steps within the analytic cluster of FIG. 5, the MRI brain scan is used to conduct an alignment to the Tailarach coordinate space (step 314). In other words, a spatial normalization step is completed. It should be appreciated that other normalization techniques or coordinate spaces (i.e., other than Tailarach) may be provided in other embodiments. In step 306, an initial EEG to MRI spatial registration may be conducted. Any past, present or future initial spatial registration technique may be utilized. This first level of registration may be conducted, and is shown as being conducted, before the brain is segmented. This registration may allow for better processing and analysis, as well as parallelization not provided by other methods. For example, with reference to FIG. 5, the brain extraction (step 316), brain segmentation (step 318) and cortical parcellation (step 320) may be conducted while parallel processing of the EEG activity relative to brain space locations (for example, steps 308, 310, 312) continues. In other words, the systems and methods of FIG. 5 advantageously allow for parallel MRI and EEG processing in a manner that also brings the data together for higher accuracy. The EEG and MRI data is brought together not only at the beginning of the process (as key inputs for the process) but is also brought together to provide for better anatomical labeling of EEG events (step 322), better source physical localization and characterization (step 324), and, ultimately, better clinical correlation decision support results (step 326).

Referring still to FIG. 5, the EEG to MRI spatial registration provided for in step 306 can be used in the step of abnormal activity detection (step 308). Abnormal activity detection (step 308) can include processing for high or low levels of energy (for example, on an absolute and/or relative basis). Source identification and localization (step 310) can be conducted in parallel with the abnormal activity detection processing (step 308). Coherence comparison map generation (step 312) can be conducted in parallel with the abnormal activity detection (step 308) and the source identification and localization (step 310). It should be noted that one or more analytic workers can be provided for each of the processing steps 308, 310, 312. For example, a different analytic worker plug-in may exist for each of the main processing steps of FIG. 5. Data can be split and multiple abnormal activity detection analytic workers (i.e., distributed parallel processes) can be processing at once.

The outputs from the processing steps 308, 310, 312 can be provided to an anatomical labeling process (step 322). In parallel with the processing conducted by processing steps 308, 310, and 312 (primarily on the EEG data), the MRI brain scan processing can continue (referring generally to the right side of FIG. 5). The brain extraction can continue in step 316. Brain extraction (sometimes referred to as skull stripping) can include defining edges, surface, brain objects, and volume extraction by processing the images. Step 316 may be entirely automated or it may operate using user feedbacks or adjustments (for example, as may be input by the user via the GUI of FIG. 2F).

Using the results from the brain extraction (step 316), processing steps including voxel-based morphometry whole brain segmentation (step 318) and surface-based morphometry cortical parcellation (step 320) may be executed. These steps may be executed in a serial fashion or in parallel (as illustrated). In an exemplary embodiment, the voxel-based morphometry can be completed using Freesurfer, an open-source software package for brain segmentation. However, as opposed to conventional Freesurfer that can take more than 40 hours to run on a desktop CPU, the Freesurfer process can be completed much faster using the parallel processing systems and methods described herein. Different parallel analytic workers can complete varying steps of the voxel-based morphometry processing. Yet different parallel analytic workers can complete varying steps of the surface-based morphometry for cortical parcellation. The plug-in based parallel processing systems and methods described above can be used with a segmentation package other than Freesurfer. Indeed, plug-ins for a different brain segmentation package could be utilized such that rapid and consequence free swapping of brain segmentation packages could occur.

Referring still to FIG. 5, a morphometric quantification step 328 can be executed to combine results from the morphometric processes 318 and 320. Averaging, confidence-based selection, or other statistical methods can be used in quantification step 328. As shown, the results from morphometric quantification 328 can be fed back into process steps 308, 310 and 312 (for example, for refining position for GUI display).

Using the results of the morphometric quantification, as well as information from processes 308-312, anatomical labelling is shown as continuing (step 322). Anatomical labeling can include using the morphometric segmentation quantification to adjust or refine labeling of abnormal activity locales, source identification locales, and coherence comparison map locales based on the MRI data. Results from the anatomical labeling (step 322) can also be stored in memory for use in generating GUI labels of locales and/or other elements shown with respect to the anatomy on the user interfaces described herein. Results from the anatomical labeling (step 322) can also be provided to a process for conducting further source localization and characterization (step 324). This step can conduct detailed processing to adjust the locales of electrode identified source events relative to the brain anatomy as defined by the MRI segmentation. The results (step 326) from this step can be used to make adjustments to GUI images (for example, the GUI of FIG. 2A), generate the GUI images, provide location reports, locate heat maps on the MRI objects of FIG. 2F, store in memory for later processing use, or to conduct other reports. One or more automated characterization processes may also or alternatively be run at step 324. For example, based on the MRI information, together with combined metrics from the abnormal activity detector, the source identification and localization process, and/or the coherence comparison maps, a script or other process can determine that there is a high probability of brain injury at a certain location in MRI segmentation space.

The integration of MRI with EEG for source localization can provide benefits. The steps of FIG. 5 may be provided by varying algorithms. Such algorithms may utilize the inverse model of overdetermined models for EEG dipolar signals, underdetermined models for distributed EEG source models via minimum norm, weighted minimum norms, laplacian weighted minimum norm (LORETA), local autoregressive averages (LAURA), epifocus approaches, Bayesian approaches, or other processing algorithms. MRI head models may be generated via isosurface construction and tessellation which can then be used as input to the definition of the solution space for EEG electrode positioning. LORETA has been shown to correctly reproduce deep sources well. However, LORETA may be sensitive to noise in the signal. Advantageously, an embodiment of the process described herein can include performing EEG source analysis on a time-frequency representation of the EEG signal to better separate noise from the signal, resulting in a more accurate representation. In some embodiments of the present systems and methods, cortical potential imaging methods using boundary element method (BEM) and finite element method (FEM) techniques can be used to reduce the number of unknowns. Regarding the BEM method, multiple shells of different conductivities can be segmented in the MRI image and triangulated into finer pieces. A linear relation between the scalp potentials and the cortical potentials can be found by applying Green's second identity within the volume between the epicortical and scalp surfaces. The cortical potentials can then be constructed by applying inverse techniques.

In an exemplary embodiment, diffusion tensor imaging (DTI imaging) may be used in place of traditional MRI segmentation in the system and method of FIG. 5. DTI imaging is a form of magnetic resonance imaging that provides for the measurement of the restricted diffusion of water in tissue in order to produce the neural tract images instead of using this data solely for the purpose of assigning contrast or colors to pixels in a cross sectional image. The analysis may follow disease affecting morphometry from white matter tracts to cortical grey matter and/or subcortical structures to get a closer diagnostic rather than using such outputs separately.

In an exemplary embodiment, PET may be used as the imaging technique. PET produces a three-dimensional image or picture of functional processes in the body. The PET system detects pairs of gamma rays emitted indirectly by a positron-emitting radionuclide (tracer), which is introduced into the body on a biologically active molecule. Three-dimensional images of tracer concentration within the body are then constructed via computer analysis. In yet another exemplary embodiment, SPECT is used as the imaging technique. Such a technique can use nuclear medicine tomographic imaging using gamma rays. In the case of PET or SPECT, the use of radionuclide may provide for better localization of cancerous cells. With segmentation, the source can be mapped to the associated cranial structures for the purpose of labeling and disease detection. PET, SPECT, or CT may be used in conjunction with MRI and not necessarily as an imaging method instead of traditional MRI. CT and MRI images may be registered to one another in order to take advantage of the combined image information/comparative analysis available to the user. In the same or yet other embodiments, PET and SPECT outputs may be overlaid on top of the CT or MRI scan. Parallel processing (for example, using a similar approach as described above) can be used to speed up and provide combinational analysis benefits.

An electrocardiogram (ECG) can provide an interpretation of the electrical activity of the heart over time. This activity can be detected by electrodes attached to the surface of the skin (for example, near the heart). A filter may be applied to the data to remove certain noise artifacts from the ECG and to detect Q wave, R wave and S wave (QRS) complexes, which allow computation of RR intervals. An arrhythmia is any abnormal cardiac rhythm. Systems and methods of the present application may be used to detect such arrhythmias using the ECG feature. Types of arrhythmias include ectopic beats, tachycardia, fibrillation, conduction blocks, bradycardia, and escape rhythms. The QRS detection method as well as a variety of spectral methods may be used to identify such conditions. Beat-to-beat statistics produced from such methods can be returned to the user after the ECG signals are processed. The ECG can also reveal abnormalities such as metabolic disturbances and structural abnormalities.

Figure 6:
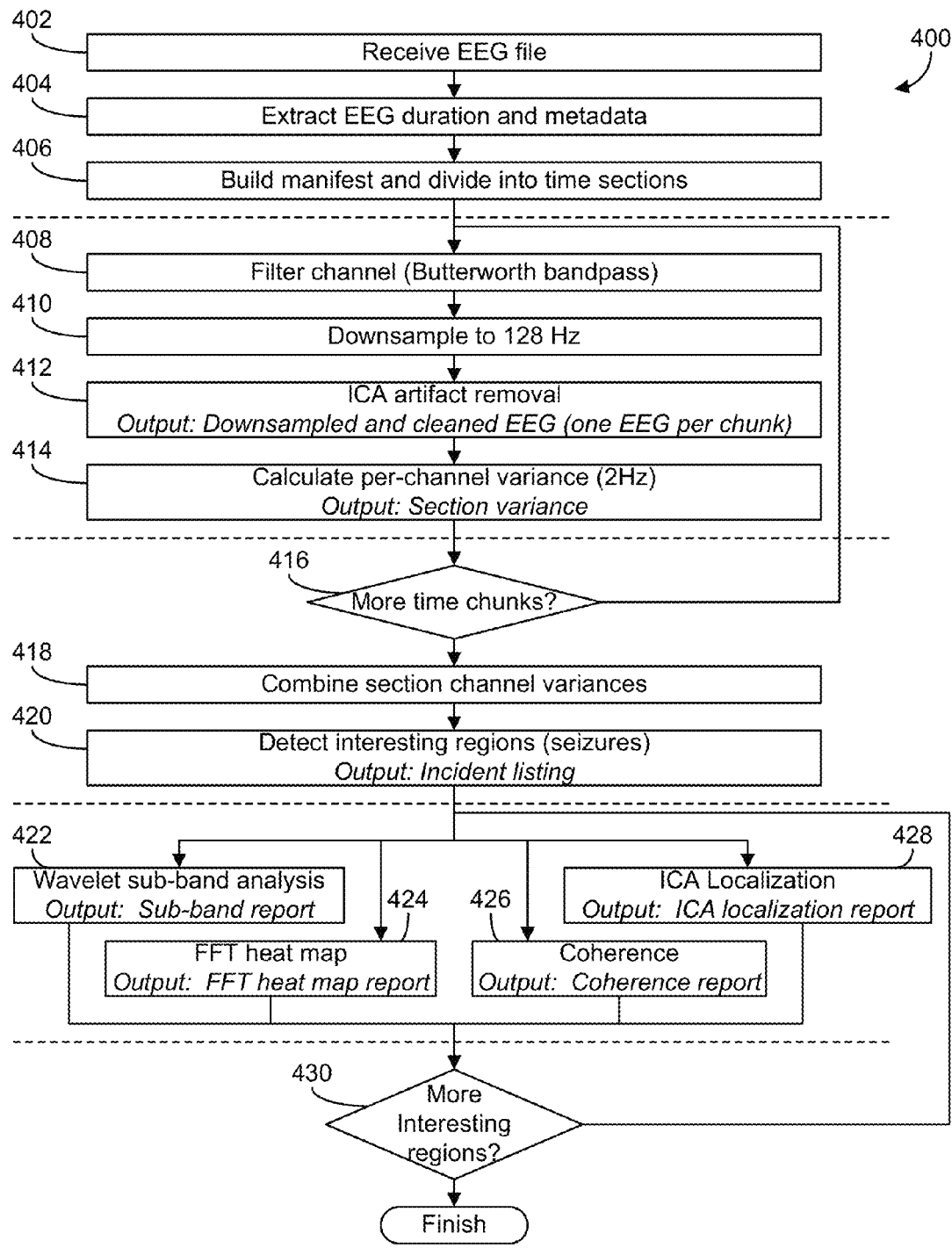
FIG. 6 illustrates a flowchart of an EEG seizure diagnostic workflow.

Referring now to FIG. 6, a flowchart of an EEG seizure diagnostic workflow 400 (i.e., process executable by the workflow-based systems and methods described above) is shown, according to an exemplary embodiment. Workflow 400 is shown to include receiving an EEG file (step 402). This reception can be completed, for example, as described above and also below with respect to FIG. 7. Workflow 400 further includes extracting EEG duration and other metadata (step 404) from the received data. This information may be used to assist with building a manifest and dividing the EEG data into time sections (step 406). The division into time sections and keeping a manifest facilitates parallelization. Each time section (i.e., time chunk) can be processed in parallel in steps 408-414 by analysis workers (for example, cloud based parallelization). Steps 408-414 may further be parallelized by channel. Thus, each electrode channel may be broken into time chunks and subjected to the processing steps 408-414.

Step 408 includes filtering the channel. This filtering may be conducted using a bandpass filter to reduce the frequency range under investigation. The bandpass filter may have end points of 0.5 Hz to 60 Hz, allowing this range to pass for further evaluation. In some embodiments, the bandpass filter may be a combination of a lowpass filter and a highpass filter. In some embodiments, the width of the pass band can be configured via administrative settings.

Step 410 includes downsampling the EEG signal. For example, if the original signal was recorded at a sampling rate of 10 KHz (corresponding to a signal data point every 0.1 milliseconds), the signal can be downsampled to, for example, 256 Hz, which corresponds to one data point every 3.90625 milliseconds. The downsampling may also be conducted to 128 Hz (corresponding to one data point every 7.8125 milliseconds). Downsampling to a lower frequency reduces the size of the data being used and can be advantageous. Downsampling to other frequencies may be conducted according to other embodiments. In yet other embodiments, the data is already at an appropriate sampling frequency when received by the system, thus no downsampling is utilized. Individual channels may have varying sampling rates, thus each channel may be downsampled individually. Filtering before downsampling may reduce or eliminate aliasing.

Step 412 includes conducting ICA artifact removal. A notch filter at 60 Hz may remove frequencies associated with the artifacts caused by electrical power lines and other interferences (for example, caused by external electrical appliances near the patient). At the end of step 412, the output for each 412 process is a downsampled and cleaned EEG (one EEG per chunk). Step 412 may include additional cleaning or filtering for content other than 60 Hz energy. For example, kurtosis, a measure of the "peakedness" of the probability distribution of a real-valued random variable, may be used to detect unusually peaked distributions of values (for example, as might happen during eye blink artifacts, AC and DC artifacts, induced line noise from electrical machinery, lighting fixtures and loose electrical contacts, etc.).

To detect unusually "peaked" distributions of potential values, kurtosis may be calculated for each data signal over the time range used in event detection window. If all activity values are similar, or the values alternate between two or more extremes, the kurtosis will be highly negative. This type of activity is not typical of brain EEG signals. Strong negative kurtosis values usually reflect AC (alternating current) or DC (direct current) artifacts, for example those induced by screen currents, strong induced line noise from electrical machinery, lighting fixtures, or loose electrode contacts. If the kurtosis is highly positive, the activity distribution is highly peaked (usually around zero) with infrequent appearance of extreme values, and the identified data is likely to contain an artifact. In some embodiments, in initial bad channel removal, any signal with a kurtosis over 5 or less than −5 can be removed and thus does not contribute to pre-calculation of statistical parameters, such as variance and mean value. In an exemplary embodiment, using a kurtosis threshold of two, bad segments of a channel can be removed.

Step 414 utilizes the output of step 412 to calculate per-channel (for example, 2 Hz) variance. When process 400 is used to detect high energy regions of an EEG characteristic of seizures on EEG recordings, a variance can be used with a sliding window. The cleaned up measurements undergo a variance measurement, for example, every 10 seconds.

Step 416 determines whether there are more time chunks of a set for analysis. If more time chunks are to be analyzed, the process loops and steps 408-414 operate on a new time chunk.

At step 418, section channel variances are combined. Once the section channel variances are combined, one or more processes (step 420) may be executed to detect incident regions. In an embodiment where seizures are detected, if the average variance of a majority of channels exceeds a threshold value based on the average energy of the lowest activity regions of the whole data (for example, a factor of 3-5) for at least 10 seconds on the majority of the channels, the EEG data has a strong indication of a generalized seizure. For example, the threshold may be 7000 microvolts^2. Step 420 can end with an incident listing and/or return the times during which the seizure occurred. Each interesting region (for example, as identified as being associated with an incident) may be analyzed further. As shown in steps 422, 424, 426 and 428, the regions can be subject to wavelet subband analysis, an FFT heat map generation and analysis, a coherence report generation and analysis, and an ICA localization report generation and analysis. Steps 422, 424, 426, 428 may be repeated for multiple regions (step 430).

Figure 7:
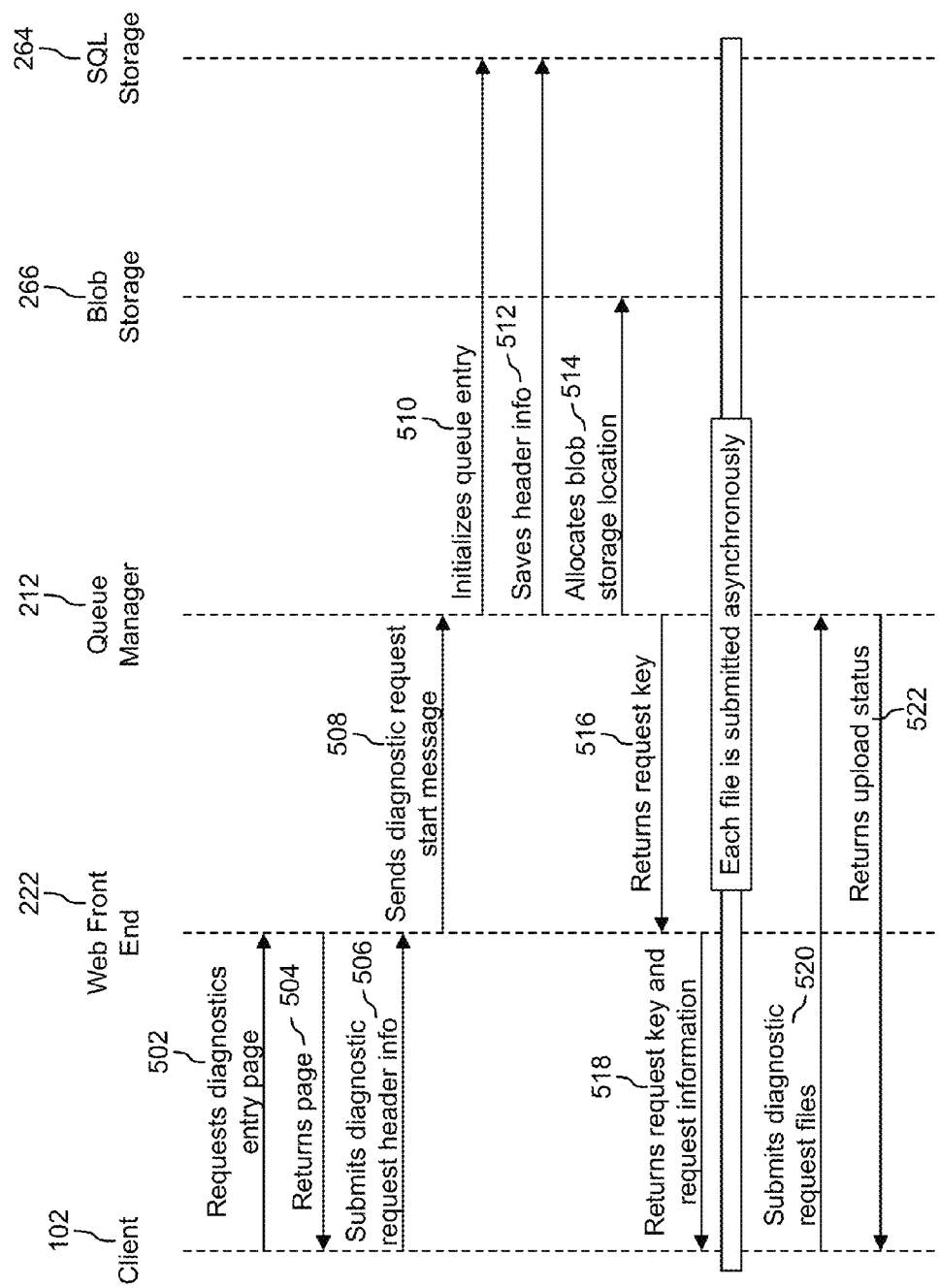
FIG. 7 illustrates a flowchart of diagnostic data submission.

Referring now to FIG. 7, a flowchart of a diagnostic data submission process is shown, according to an exemplary embodiment. The process of FIG. 7 may be used by client 102 for submitting diagnostic requests to analysis server 104. More particularly, the process of FIG. 7 may be executed to submit one or more EEG files for diagnostics.

The process of FIG. 7 includes client 102 requesting a diagnostics entry page (step 502) from the web interface. Web front end 222 of web interface 220 (as described in FIG. 1B) may process the input and return an entry page (step 504). The entry page may allow client 102 to submit information relating to the diagnostics request of the client. Client 102 may submit diagnostic request header information of an associated EEG file (step 506) to web front end 222. The header information may generally include patient information, technical specifications of EEG recording, data records of processed electrical signals generated during the EEG recording, etc.

Web front end 222 may provide a diagnostic request start message to queue manager 212 (step 508). The start message may be used by queue manager 212 to initialize a queue entry (step 510) and to store the queue entry in diagnostic queue 265 of SQL storage 264. This places the diagnostic request of client 102 in a queue for future processing. Queue manager 212 further saves header information of the EEG file in SQL storage 264 (step 512), and allocates blob storage location in blob storage 266 for the request (for storing medical data of the patient relating to the diagnostics request) (step 514).

When the system is ready for processing one or more EEG files, queue manager 212 may return a request key to web interface 220 and more particularly web front end 222 (step 516). The request key and request information is then returned to client 102 (step 518) for identifying to client 102 that one or more of the diagnostic requests are ready for processing. Client 102 may then submit the diagnostic request files (step 520), and queue manager 212 receiving the files may return an upload status of the files to client 102 (step 522). Each diagnostic request file may be submitted asynchronously, i.e., intermittently, based on the queue.

Referring now to FIG. 8, an XML definition of many of the modules described herein is presented. Parameters for the modules, reports, processing steps, and the like may be stored in a definition repository such as the XML shown in FIG. 8. Processing order and/or values (for example, filter values) may be changed by changing the parameters of the document of FIG. 8.

As used herein, the singular terms "a," "an," and "the" include plural referents unless the context clearly dictates otherwise. Thus, for example, reference to an object can include multiple objects unless the context clearly dictates otherwise.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products including machine-readable media for carrying or having machine-executable instructions or data structures stored thereon. Such machine-readable media can be any available media that can be accessed by a general purpose or special purpose computer or other machine with a processor. By way of example, such machine-readable media can include RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions. Software implementations could be accomplished with standard programming techniques with rule based logic and other logic to accomplish the various connection steps, processing steps, comparison steps and decision steps.

While this specification contains many specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products embodied on tangible media. References to "or" may be construed as inclusive so that any terms described using "or" may indicate any of a single, more than one, and all of the described terms.

What is claimed is:

1. A multi-factor medical data decision support system, comprising:
    an analysis server communicatively coupled to a computing device, the analysis server comprising: (a) an analysis manager which receives medical data measured from a patient located at a remote site, the medical data comprising electroencephalogram (EEG) measurements taken from at least one of a plurality of frequency channels and a plurality of electrodes positioned on the patient's head and MRI brain segmentation results taken from the patient and (b) a web interface for communication with a client located at the remote site;
    a plurality of analytic modules coordinated by the analysis manager for analyzing the medical data by generating, concurrently with brain extraction performed by the analysis manager, a report comprising at least two of: coherences corresponding to a plurality of brain regions' EEG signal pairs, results of abnormal activity detection, and source identification and localization wherein each of the one or more coherences is calculated as the correlation coefficient of phases between a first EEG signal of the signal pair corresponding to a first brain region of the patient and a second signal of the signal pair corresponding to a second brain region of the patient, wherein each of the plurality of analytic modules is configured for independent loading and execution;
    a non-transitory storage in data communication with the analysis server and the one or more analytic modules, wherein the storage stores at least one of measured medical data and processed medical data;
    wherein the analysis manager distributes the generation of the report into a plurality of tasks to be performed by parallel analytic modules comprising: (a) calculating the one or more coherences of the plurality of brain regions' EEG signal pairs for each of the at least one of a plurality of frequency channels and a plurality of electrodes, (b) processing for high or low levels of energy to detect abnormal activity, and (c) identifying and localizing the source of the medical data being analyzed, wherein the analysis manager comprises a scheduler configured to communicate with the analytic modules to allocate the plurality of tasks to be performed in parallel to the plurality of analytic modules for independent loading and execution, wherein the analysis manager is configured to instantiate and execute the analytic modules to perform the allocated tasks in parallel;
    wherein the analysis manager divides the medical data into a plurality of time sections to be processed in parallel by the analytic modules and filters each of the plurality of time sections to remove independent component analysis (ICA) artifacts from the medical data; and
    wherein the web interface is configured to provide the report to the client located at the remote site, the report comprising graphic analysis results and at least one coherence map generated by the analytic modules by aggregating the one or more coherences corresponding to a plurality of brain regions' EEG signal pairs.

2. The system of claim 1, wherein at least one of the plurality of analytic modules is configured for combined analysis of two or more different types of medical data.

3. The system of claim 2, wherein the at least one of the plurality of analytic modules is configured for combined analysis of structural medical data and functional medical data of an organ to associate a source of an organ activity with a location in an anatomical structure of the organ.

4. The system of claim 1, wherein each of the plurality of analytic modules comprises a plurality of analytic workers each configured to perform a specific analysis, wherein each of the plurality of analytic workers is configured to be independently loaded into one of the plurality of analytic modules and independently executed.

5. The system of claim 4, wherein the web interface is configured to provide analysis results of the plurality of analytic workers to the client on a single user interface at the same time.

6. The system of claim 1, wherein at least a part of the system resides on one or more cloud servers as a virtual machine instance.

7. The system of claim 6, wherein at least a part of the system runs with at least two virtual machine instances and is configured to be dynamically scaled in response to demand.

8. A cloud-based electroencephalogram (EEG) analysis system, comprising:
    an analysis server communicatively coupled to a computing device, the analysis server comprising: (a) an analysis manager which receives medical data measured from a patient located at a remote site, the medical data comprising electroencephalogram (EEG) measurements taken from at least one of a plurality of frequency channels and a plurality of electrodes positioned on the patient's head and MRI brain segmentation results taken from the patient and (b) a web interface for communication with a client located at the remote site;
    a plurality of analytic workers managed by the analysis manager for analyzing EEG data to generate at least one of wavelet subbands, power spectrum, coherences between signals, independent component analysis, component heat maps, and density spectral map of the EEG data by generating, concurrently with the brain extraction performed by the analysis manager, a report comprising at least two of: coherences corresponding to a plurality of brain regions' EEG signal pairs, results of abnormal activity detection, and source identification and localization wherein each of the one or more coherences is calculated as the correlation coefficient of phases between a first EEG signal of the signal pair corresponding to a first brain region of the patient and a second signal of the signal pair corresponding to a second brain region of the patient;

a non-transitory storage in data communication with the analysis server and the plurality of analytic workers which stores at least one of measured medical data and processed medical data;

wherein the analysis manager distributes the generation of the report into a plurality of tasks to be performed by parallel analytic workers comprising: (a) calculating the one or more coherences of the plurality of brain regions' EEG signal pairs for each of the at least one of a plurality of frequency channels and a plurality of electrodes, (b) processing for high or low levels of energy to detect abnormal activity, and (c) identifying and localizing the source of the medical data being analyzed, wherein the analysis manager comprises a scheduler configured to communicate with the analytic workers to allocate the plurality of tasks to be performed in parallel to the plurality of analytic workers for independent loading and execution;

wherein the analysis manager divides the medical data into a plurality of time sections to be processed in parallel by the analytic workers and filters each of the plurality of time sections to remove independent component analysis (ICA) artifacts from the medical data;

wherein the web interface is configured to provide the report to the client located at the remote site, the report comprising graphic analysis results and at least one coherence map generated by the analytic workers by aggregating the one or more coherences corresponding to a plurality of brain regions' EEG signal pairs; and wherein at least a part of the system resides on one or more cloud servers as a virtual machine instance.

9. The system of claim 8, wherein the system further comprises an analytic cluster configured to perform combined analysis of the EEG data and at least one of magnetic resonance image (MRI) data, computed tomography (CT) data, magnetoencephalography (MEG) data and electrocardiogram (ECG) data.

10. The system of claim 8, wherein the analysis manager is configured to divide the EEG data into time sections and keep a manifest in the remote storage for parallel processing.

* * * * *